(12) United States Patent
Hardaway

(10) Patent No.: US 8,412,538 B2
(45) Date of Patent: *Apr. 2, 2013

(54) SYSTEM AND METHOD FOR PREPURCHASED REPLENISHMENT OF PHARMACEUTICALS

(75) Inventor: Jason Michael Hardaway, Portland, OR (US)

(73) Assignee: Wellpartner Incorporated, Portland, OR (US)

( * ) Notice: Subject to any disclaimer, the term of this patent is extended or adjusted under 35 U.S.C. 154(b) by 418 days.

This patent is subject to a terminal disclaimer.

(21) Appl. No.: 12/481,449

(22) Filed: Jun. 9, 2009

(65) Prior Publication Data

US 2010/0312578 A1    Dec. 9, 2010

(51) Int. Cl.
  *G06Q 10/00* (2012.01)
  *G06Q 50/00* (2012.01)
(52) U.S. Cl. .................................. 705/2; 705/3
(58) Field of Classification Search .................. 705/2, 3
  See application file for complete search history.

(56) References Cited

U.S. PATENT DOCUMENTS

| | | | |
|---|---|---|---|
| 6,021,392 A | 2/2000 | Lester et al. | |
| 6,055,507 A | 4/2000 | Cunningham | |
| 6,219,587 B1 * | 4/2001 | Ahlin et al. | 700/233 |
| 7,640,170 B1 | 12/2009 | Gourley | |
| 7,797,171 B2 * | 9/2010 | Reardan et al. | 705/2 |
| 7,996,243 B1 * | 8/2011 | Ali et al. | 705/2 |
| 2001/0037216 A1 | 11/2001 | Oscar et al. | |
| 2002/0002495 A1 | 1/2002 | Ullman | |
| 2002/0069088 A1 | 6/2002 | Berg | |
| 2002/0188469 A1 * | 12/2002 | Shalmi et al. | 705/2 |
| 2003/0088333 A1 * | 5/2003 | Liff et al. | 700/237 |
| 2004/0145472 A1 * | 7/2004 | Schmidtberg et al. | 340/539.27 |
| 2004/0230502 A1 | 11/2004 | Fiacco et al. | |
| 2006/0184391 A1 | 8/2006 | Barre et al. | |
| 2007/0233517 A1 | 10/2007 | Dayal | |
| 2007/0233522 A1 | 10/2007 | Dayal | |
| 2008/0235050 A1 | 9/2008 | Hallberg | |
| 2008/0288281 A1 | 11/2008 | Shell et al. | |
| 2009/0281823 A1 | 11/2009 | Hardaway | |
| 2011/0054935 A1 | 3/2011 | Hardaway | |

OTHER PUBLICATIONS

Non-final Office Action for U.S. Appl. No. 12/145,960, filed Jun. 25, 2008, mailed from the USPTO on Apr. 1, 2011, 25 pgs.
Non-final Office Action for U.S. Appl. No. 12/117,447, filed May 8, 2008, mailed from the USPTO on Jun. 22, 2010, 10 pgs.
Final Office Action for U.S. Appl. No. 12/117,447, filed May 8, 2008, mailed from the USPTO on Jan. 5, 2011, 12 pgs.
Non-final Office Action for U.S. Appl. No. 12/117,467, filed May 8, 2008, mailed from the USPTO on Feb. 3, 2011, 11 pgs.

(Continued)

*Primary Examiner* — Neha Patel
(74) *Attorney, Agent, or Firm* — John R. Thompson; Stoel Rives LLP

(57) ABSTRACT

A computer system and method manages the disbursement and replacement of medication units to patients. Medication units disbursed to qualified patients under qualified discount plans are replaced by replenishment. Computer systems implementing traditional replenishment, cached replenishment, and prepurchased replenishment are disclosed. The computer system and method monitors medication units disbursed to patients by a pharmacy and tracks the amount of medication units disbursed to qualified patients of health care providers qualified under a discount program. When the amount of disbursed medication units reaches a threshold, replacement medication units are ordered. The medication units disbursed to non-qualified patients are replaced through restocking and the medication units disbursed under a qualified discount program are replaced through traditional replenishment, cached replenishment, and/or prepurchased replenishment.

30 Claims, 13 Drawing Sheets

OTHER PUBLICATIONS

Office Action for U.S. Appl. No. 12/552,198, filed Sep. 1, 2009, mailed from the USPTO on Nov. 25, 2011, 19 pgs.
Notice of Allowance for U.S. Appl. No. 12/117,467, filed May 8, 2008, mailed from the USPTO on Sep. 8, 2011, 8 pgs.
Office Action for U.S. Appl. No. 12/145,960, filed Jun. 25, 2008, mailed from the USPTO on Dec. 12, 2011, 24 pgs.
Anonymous, "GPO Access Solution: An Overview of Group Purchasing and Own Use", 2005, Wellpartner, 31 pgs.
Anonymous, "340B Access Solution: An Overview of the 340B Discount Drug Program", 2004, Wellpartner, 42 pgs.
Anonymous, "Access Solutions," Website printout, archived Jul. 11, 2006, 1 pg.
Office Action for U.S. Appl. No. 12/552,198, filed Sep. 1, 2009, mailed from the USPTO on May 8, 2012, 15 pgs.
Office Action for U.S. Appl. No. 12/117,447, filed May 8, 2008, mailed from the USPTO on May 7, 2012, 18 pgs.
Advisory Action for U.S. Appl. No. 12/145,960, filed Jun. 25, 2008, mailed from the USPTO on May 21, 2012, 3 pgs.
Office Action for U.S. Appl. No. 12/145,960, filed Jun. 25, 2008, mailed from the USPTO on Jan. 17, 2013, 30 pgs.

* cited by examiner

SYSTEM AND METHOD FOR PREPURCHASED REPLENISHMENT OF PHARMACEUTICALS

TECHNICAL FIELD

This disclosure relates generally to techniques for managing the dispersal and replenishment of pharmaceutical inventories.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION OF PREFERRED EMBODIMENTS

Figure 1:
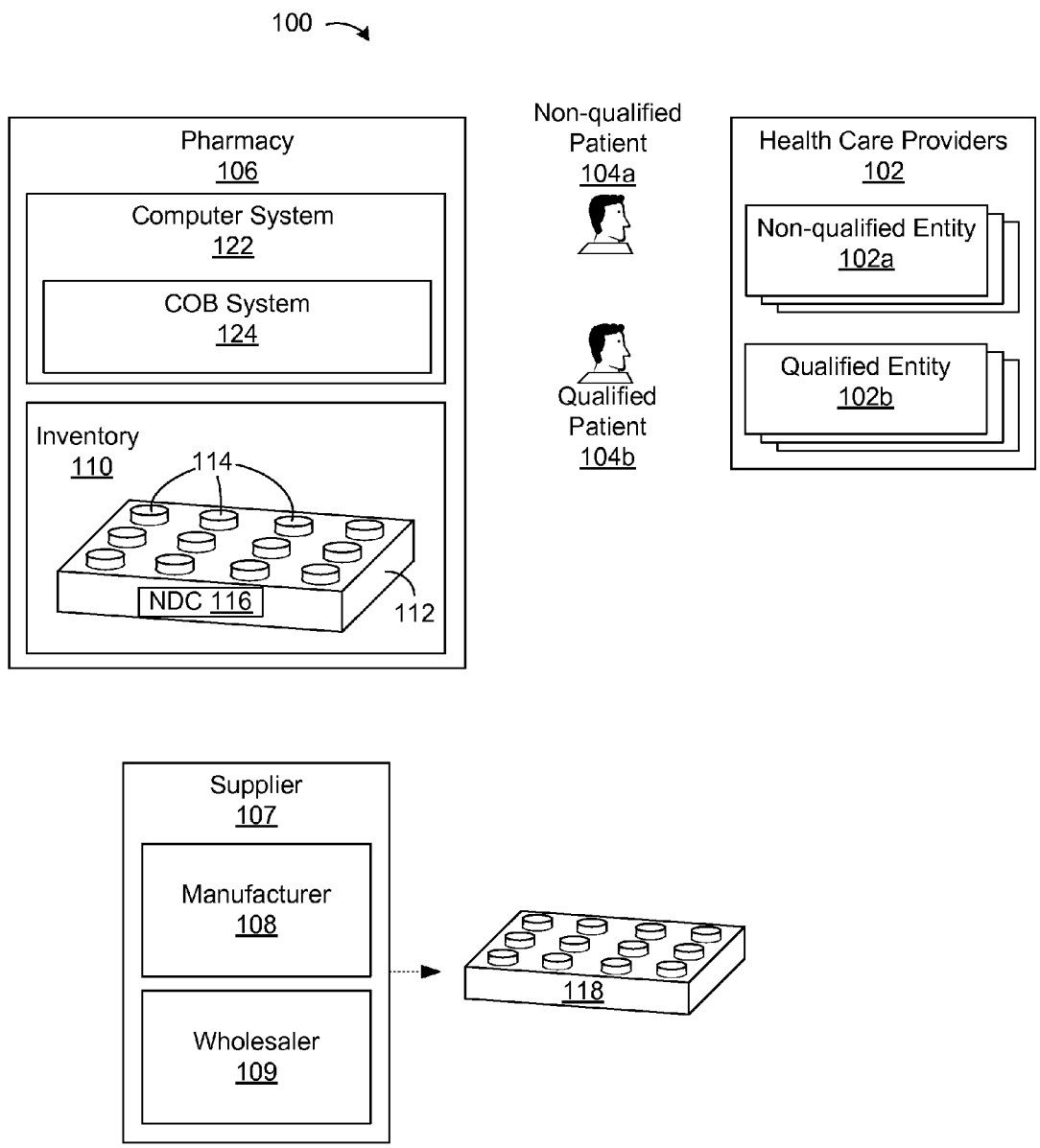
FIG. 1 is a block diagram of a system for disbursing and restocking medications, according to one embodiment.

A number of drug discount programs are available to certain qualified entities. These drug discount programs include the federal 340B program (hereafter "340B program" or "340B"), also known as section 602 or "PHS" pricing, purchasing cooperatives commonly referred to as Group Purchasing Organizations (GPOs), and Patient Assistance Programs (PAPs).

The 340B program is a federally administered program that allows certain eligible health care providers 102 ("Covered Entities") within the health care safety-net to purchase outpatient medications from manufacturers at or below a defined discount price. The 340B program is not a governmental purchasing program, but is a discount program administered by the Federal Government. Pharmaceutical manufacturers are required to sell covered medications to qualified entities at or below a statutorily defined "ceiling price" as a condition for Medicaid participation. The 340B program is discussed in greater detail below with reference to FIG. 1.

Group Purchasing Organizations (GPOs) are purchasing cooperatives in which organizations with non-profit status can participate. The Nonprofit Institutions Act (15 U.S.C.A. 13c) exception to the Robinson-Patman Act permits some organizations to take advantage of their status as non-profit institutions to purchase products, including pharmaceutical drugs, for their employees, retirees, dependents and other eligible individuals by participating in a GPO. A GPO eligible entity realizes significant drug discounts on pharmaceutical drugs purchased for its "own use."

Patient Assistance Programs (PAPs) may also provide significant drug discounts to consumers. PAPs are run by pharmaceutical companies to provide free medications to people who cannot afford to buy their medicine. There are over 1000 PAPs offered with varying criteria for eligibility.

Discount drug programs may be referred to generally as "qualified programs," and a health care provider covered by such a program may be referred to as a "qualified entity." A Covered Entity under the 340B program is a type of qualified entity, as the term qualified entity is used herein. The common thread of the aforementioned qualified programs is that each can provide significant drug discounts to eligible patients when properly utilized. Although the 340B, GPO, and PAP discount programs are specifically mentioned, these programs are merely examples of qualified programs. The teachings of this disclosure may extend to any discount program and related regulatory scheme. As such, this disclosure should not be read as limited to any particular set of qualified programs and/or any particular set of qualified entities.

Qualified programs generally are heavily regulated, and the complexity of regulations renders many qualified entities and retail pharmacies unable to support these programs. The regulations often mandate complex inventory management and payment schemes to prevent such unethical practices as diversion of discounted products and double-dipping of discounts and government rebates. Moreover, the regulations are strict, imposing heavy penalties for violation. In some cases, failure to follow the regulations of a particular qualified program may constitute a criminal offense and result in disbarment from participation in qualified programs, including Medicare and/or Medicaid. Consequently, complying with these regulations can demand large overhead, and for the unsophisticated qualified entities and retail pharmacies, the regulatory structure of such programs presents an untenable risk. As a result, such qualified entities are in the unique position of having access to significant discount pricing of pharmaceutical drugs, but are largely unable to manage the burden of complying with such programs.

The level of savings available through the discounts offered by qualified programs, however, makes supporting these programs highly desirable. Unique systems and methods can be implemented to enable retail pharmacies to participate in qualified programs and to report, manage inventory, and replenish inventory in compliance with the mandated regulations.

A computer program, for example, can be designed and implemented to provide the required functions in accordance with the regulations to enable retail pharmacies to participate in these discount programs. As another example, a "plug-in" module to extend the functionality of the Coordination of Benefits (COB) systems that are already in wide use among retail pharmacies can be similarly designed and implemented to fulfill the regulatory requirements of qualified programs. Still another example is a system running on another computer that interfaces with the COB system and/or computer system running the COB system.

The present disclosure provides an improved system and method to enable a pharmacy to appropriately replace dispensed inventory, either by replenishment or by restocking. According to one aspect of the present disclosure, the systems and methods disclosed facilitate cached replenishment to improve inventory management of a pharmacy that sells medications to both qualified patients of qualified entities and to non-qualified patients. The systems and methods disclosed can enable the pharmacy to properly replace pharmaceuticals sold to qualified patients of qualified entities participating in one or more qualified programs while tracking and maintaining the integrity of the inventory for each such program. Replacement of pharmaceuticals sold to qualified patients of qualified entities can be accomplished through a process that can be referred to as replenishment. As previously mentioned, the systems and methods can be implemented as part of a stand-alone system, as an adaptation or plug-in for an existing system such as a COB system, or as a separate system interfacing with an existing system such as a COB system.

According to another aspect of the present disclosure, the systems and methods can also enable the pharmacy to appropriately replace pharmaceuticals sold to non-qualified patients, without overstocking due to inventory replaced through replenishment. Replacement of pharmaceuticals sold to non-qualified patients can be accomplished through traditional restocking. The systems and methods coordinate a cached replenishment with a drug manufacturer and/or wholesaler to replace pharmaceuticals sold to qualified patients of qualified entities participating in a qualified program. The coordination of the cached replenishment prevents the pharmacy from inadvertently 'over ordering' inventory when an order is placed to replace inventory dispensed under a qualified program. As previously mentioned, the systems and methods can be implemented as part of a stand-alone system, as an adaptation or plug-in for an existing system such as a COB system, or as a separate system interfacing with an existing system such as a COB system.

According to another aspect of the present disclosure, the systems and methods can enable a pharmacy to virtually replenish inventory that will be sold in the future under a qualified discount plan. Prepurchased replenishment allows a pharmacy to leverage limited-duration advantageous pricing periods, by pre-ordering anticipated inventory replenishment at deeper discount pricing available during such advantageous pricing periods. The systems and methods monitor for limited duration advantageous pricing and then pre-order prepurchased replenishment containers according to anticipated inventory replenishment requirements, purchasing prepurchased replenishment containers at the advantageous pricing. The systems and methods coordinate prepurchased replenishment credit with a drug manufacturer and/or wholesaler, on behalf of the pharmacy, for pre-ordered replenishment inventory. Accordingly, when the replenishment threshold for that medication is met, the pharmacy receives a replacement container through replenishment at the advantageous pricing. As previously mentioned, the systems and methods can be implemented as part of a stand-alone system, as an adaptation or plug-in for an existing system such as a COB system, or as a separate system interfacing with an existing system such as a COB system.

The described features, structures, or characteristics may be combined in any suitable manner in one or more embodiments. Those skilled in the art will recognize that the invention can be practiced without one or more of the specific details, or with other methods, components, materials, etc. In other instances, well-known structures, materials, or operations are not shown in detail to avoid obscuring aspects of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawing or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable storage medium having stored thereon instructions that may be used to program a computer (or other electronic device) to perform processes described herein. The machine-readable storage medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer may function both as a client and as a server. Each network includes at least two computers, such as the server and/or clients. A computer may be a workstation, laptop computer, disconnectable mobile computer, server, mainframe, cluster, so-called "network computer" or "thin client", personal digital assistant or other hand-held computing device, "smart" consumer electronics device or appliance, or a combination thereof.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, satellites, microwave relays, modulated AC power lines, physical media transfer, and/or other data transmission "wires" known to those of skill in the art. The network may encompass smaller networks and/or be connectable to other networks through a gateway or similar mechanism.

Each computer includes at least a processor and a memory; computers may also include various input devices and/or output devices. The processor may include a general purpose device, such as an Intel®, AMD®, or other "off-the-shelf" microprocessor. The processor may include a special purpose processing device, such as an ASIC, PAL, PLA, PLD, Field Programmable Gate Array, or other customized or programmable device. The memory may include static RAM, dynamic RAM, flash memory, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computers may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as: general purpose computers; computer programming tools and techniques; computer networks and networking technologies; digital storage media; authentication; access control; and other security tools and techniques provided by public keys, encryption, firewalls, and/or other means.

FIG. 1 is a block diagram of a system 100 for disbursing and restocking medications. The participants include health care providers 102, patients 104, pharmacies 106, and pharmaceutical suppliers 107 (e.g., manufacturers 108 and wholesalers). The health care providers 102 provide health care services to patients 104. Medications are dispensed to a patient 104 through the use of one or more pharmacies 106 under the supervision of a health care provider 102. Depending on the arrangement, the pharmacy 106 may provide medications to a health care provider 102 or may provide medications directly to a patient 104. The pharmacy medication inventory 110 that is disbursed is replaced by placing orders with pharmaceutical suppliers 107. The suppliers 107 can include manufacturers 108 and/or wholesalers 109. The inventory 110 disbursed under a qualified program can be replaced through a replenishment model and inventory 110 disbursed to nonqualified customers can be replaced through traditional restocking procedures, as discussed in greater detail below with reference to FIGS. 3, 5, and 7.

The pharmacy 106 has an inventory 110 of medications. In an inventory 110, containers 112 include a quantity of medication units 114. The medication units 114 are discrete units and may be dispensed to a patient 104 and/or a health care provider 102. A container 112 has a corresponding national drug code (NDC) 116, or other identifying code. Typically an NDC 116 comprises eleven digits, with the first nine digits identifying the type of medication and the last two digits identifying the number of medication units 114 in the container 112. For example, a medication "Feel Good" may be identified by an NDC 116 having the first nine digits 123234345. If Feel Good is sold in a container 112 that is a bottle of one hundred medication units, the corresponding NDC 116 may be 123234345-11. If Feel Good is sold in a container 112 of ten medication units, the corresponding NDC may be 123234345-10.

A pharmacy 106 will try to maintain enough inventories 110 to meet all the demands of its patients, clients, and customers, while attempting to minimize shelf space. Shelf space at a pharmacy 106 is very limited and to the extent it draws from other retail floor space, can be costly. Moreover, some medications have a shelf life and, if not dispensed, expire and must be discarded. To minimize shelf space and expiration of medications, a pharmacy may establish inventory thresholds to dictate minimum and maximum inventory levels. A maximum threshold may dictate the maximum number of medication units 114 on hand at any given time. A maximum threshold may be determined based on shelf space and/or projected dispensing of the medication. A replacement threshold may be established to dictate the number of medication units 114 to be dispensed before an order is placed with a manufacturer 108 or wholesaler 110 to replace the inventory. Once the replacement threshold number of medication units has been dispensed, an order is placed. A replacement threshold is generally a multiple of a fill level. A fill level is the minimum number of containers 112 that can be ordered for a given NDC 116, as established by a supplier 107, whether a manufacturer 108 or a wholesaler 109. A fill level may enable a supplier 107 to achieve economies of scale. A fill level may be determined based on the characteristics of the medication and/or constraints of practical shipping of the medication.

As an example of inventory thresholds, if a first supplier 107 distributes a medication "Feel Good" with an NDC 116 corresponding to a container 112 that is a bottle of one hundred medication units 114, the supplier 107 may establish a fill level of one bottle for the medication Feel Good. The minimum order for that particular NDC 116 from that first supplier 107 is one bottle. The pharmacy 106 may decide that it should replace its inventory of the Feel Good medication every time a full bottle is distributed, and accordingly the pharmacy can establish a replacement threshold of one bottle. When one hundred medication units 114 of Feel Good are dispensed, an order of one bottle is placed with the first supplier 107 to replace the dispensed medication units 114 of Feel Good. As will be appreciated, in this example, the replacement threshold of the pharmacy 106 could be two bottles, or any number of bottles.

A second supplier 107 may choose to sell the same medication Feel Good with an NDC 116 corresponding to a container 112 that contains ten medication units 114. To achieve economies of scale, the supplier 107 may establish a fill level of five containers. Thus, the minimum order for "Feel Good" with that particular NDC 116 is five containers 112. The pharmacy 106 may determine that it needs to replace its inventory for the medication "Feel Good" when 100 medication units 114 are dispensed. Accordingly, the pharmacy 106 may establish a replacement threshold of ten containers for Feel Good with that particular NDC 116.

As another example, consider a medication "EZInhale" sold in a container 112 that is a single inhaler. Accordingly, there is also only one medication unit 114 (i.e. inhaler) per container 112. To achieve economies of scale, a supplier 107 may establish a fill level of five. EZInhale may be an extremely popular medication with an extremely long shelf life. A pharmacy may sell ten EZInhale inhalers in any given week. A replacement order may take a full week to receive. Accordingly, the pharmacy 106 may establish a maximum threshold of thirty inhalers, due to the demand, and a replacement threshold of ten, so as to always have at least ten inhalers on hand in the event a replacement order is delayed a week.

As can be appreciated from these examples, the scenarios for disbursing and replacing medication inventory are numerous and varied. A person of ordinary skill in the art will appreciate that the scenarios provided are merely illustrative, and the present disclosure is not to be limited in any way by any particular dispensing or replacement scenario, or any particular thresholds that may be established to manage inventory. In one embodiment, a minimum threshold may be established, rather than a replacement threshold and/or a maximum threshold. Still other thresholds may be established as well.

Some of the health care providers 102 may be qualified entities 102b that are eligible to participate in one or more discount programs (i.e., qualified programs). As mentioned above, these qualified programs include, but are not limited to Group Purchasing Organizations (GPOs), Patient Assistance Programs (PAPS), and the 340B program. Participation in these programs can significantly impact pricing of the health care provided by qualified entities to qualified patients 104b, including any medications dispensed to such qualified patients 104b. Health care providers 102 that are not eligible to participate in a discount program are referred to herein as non-qualified entities 102a.

The 340B program, for example, can significantly impact the pricing of medications. The 340B program is a federally administered program that allows certain eligible health care providers, or qualified entities 102b, within the health care safety-net to purchase outpatient medications from manufacturers at or below a defined discount price. These eligible health care providers are also referred to as "Covered Entities." A Covered Entity is also one type of "qualified entity 102b," as the term is defined above and used herein. For sake of simplicity in referring to the Figures, Covered Entities will be referred to in the more general sense as qualified entities 102b, although it will be appreciated that the term "qualified entities" encompasses more than simply Covered Entities under the 340B program.

Eligibility for participation in a 340B program is determined by entity status, specifically by receiving one of several grants or by being a certain type of Disproportionate Share Hospital or Federally Qualified Health Center (FQHC) or look-alike. Eligible entities can participate in the 340B program as qualified entities 102b. Eligible entities include core health care safety-net providers and a number of health facilities. Health care safety-net providers deliver care to low-income and other vulnerable populations, including the uninsured and those covered by Medicaid. Many of these safety-net providers have either a legal mandate or an explicit policy to provide services regardless of a patient's ability to pay. Major safety-net providers include public hospitals and community health centers and clinics, as well as teaching and community hospitals, private physicians, and other providers who deliver a substantial amount of care to these populations.

Various Federally Qualified Health Centers (FQHCs) can also be eligible entities under 340B. FQHCs include Consolidated Health Centers, Migrant Health Centers, Health Care for the Homeless Programs, school-based health centers, Public Housing Primary Care Programs, PL 93-638 tribal health centers, urban Indian health centers, and qualified community health clinics. FQHC look-alikes can also be eligible entities under 340B. FQHC look-alikes are organizations that meet all of the eligibility requirements of an organization that receives a PHS Section 330 grant, but does not receive grant funding.

Other entities that may be eligible under 340B may include, native Hawaiian health centers, Ryan White Care Act Grantees, Title X Family Planning, black lung clinics, comprehensive hemophilia diagnostic treatment centers, state or locally funded centers treating sexually transmitted diseases or tuberculosis, certain disproportionate share hospitals, and other safety-net organizations.

In administering the 340B program, the Federal Government requires that pharmaceutical suppliers 107, both manufacturers 108 and wholesalers 109, sell covered medications to qualified entities 102b at or below a statutorily defined "ceiling price" as a condition for Medicaid participation. Covered medications may include any medication reimbursed by Medicaid, including prescription or over-the-counter medications. The 340B price is the ceiling price, meaning it is the most that qualified entities 102b can be charged for medications purchased directly from manufacturers 108. In compliance with statutes, the ceiling price may be derived from Medicaid pricing. The qualified entities 102b are allowed, and even encouraged, to negotiate sub-ceiling prices with drug suppliers 107. Accordingly, the qualified entities 102b can realize substantial cost reductions on medications used for qualified patients 104b in an outpatient setting.

The qualified entities 102b may provide 340B pharmacy access for their patients 104 through one of three methods. A first method is a clinic dispensary, or an on-site pharmacy 106 in the form of a dispensing cabinet, that utilizes a small inventory 110 of basic medications. A second method is a full-service, in-house pharmacy 106 created and operated by the qualified entity 102b on its premises. A third method is a contracted pharmacy 106 which is an external pharmacy under contract with the qualified entity 102b to provide pharmacy services and medications to the provider 102 and/or provider's patients 104.

A qualified entity 102b may prefer to provide pharmacy services to patients by contracting with an external pharmacy. This approach allows a qualified entity 102b to offer to qualified patients 104b all of the benefits and services of a full-service pharmacy without the costs of operating a full-service in-house pharmacy. Contracting with a pharmacy can also greatly reduce the administrative burden of the qualified entity 102b to be able to make the 340B discount available to patients. In exchange for participating in the covered program as its dispensing agent, a contracted pharmacy receives a dispensing fee.

The profits that can be realized under the 340B program can be substantial. As noted above, the qualified entities 102b can freely negotiate sub-ceiling prices with drug manufacturers 108. Often the drug manufacturers 108 and the wholesalers 109 offer the qualified entities 102b deeply discounted prices (or limited duration advantageous pricing). These periods of limited duration advantageous pricing may be offered to 'blow-out' excess inventory, among other reasons. The discounts are significant, often pennies on the dollar of regular price. These discounts are offered periodically for a relatively short duration such as one or two weeks at a time. Rather than offering the deep discounts to all consumers, the drug manufacturers 108 and wholesalers 120 may prefer to further discount prices to 340B qualified entities 102b. The tight regulatory control and relative scarcity of 340B qualified entities 102b offer a relatively isolated, and thus ideal, market to which the drug manufacturers 108 and wholesalers 109 can offer the deepest discounts.

Although the potential savings and fees to be shared are substantial, the burdens shared between the qualified entity 102b and the pharmacy 106 are also substantial. Moreover, additional challenges are introduced by the contract pharmacy arrangement. For example, because the 340B program is a provider-specific medication discount program, the qualified entity 102b is the only organization that can legally purchase 340B medications, and the qualified patients 104b of the qualified entity 102b are the only people who can receive those medications. Therefore, a contract pharmacy 106 must operate under a "bill-to/ship-to" arrangement, where medications are shipped by the supplier 107 directly to the pharmacy 106, and the bill for the medications is sent to the qualified entity 102b. Coordinating payments from the qualified entity 102b to the supplier 107 to replenish inventory depleted through qualified disbursements can require significant overhead for a contracted pharmacy 106. The contract pharmacy 106 must then ensure that only qualified patients 104b receive those discounted medications The 340B program further prohibits "double-dipping." The qualified entities 102b cannot request 340B prices for the same medication for which Medicaid will request a rebate in order to prevent double-dipping. A qualified entity 102b can receive a discount through the 340B program, or Medicaid can receive a discount via rebate. However, both may not occur for the same dispensed medication units 114. The administrative burden required for a contract pharmacy 106 to prevent double-dipping can be substantial.

The 340B program also prohibits all forms of 340B medication resale or diversion. A patient 104 who receives medication through a 340B program must be a qualified patient 104b of a qualified entity 102b to help prevent diversion of 340B program products to non-qualified patients 104a. Diversion under the 340B program is the distribution of 340B medications to non-340B qualified patients 104a, either intentionally or unintentionally. The qualified entity 102b may not resell or transfer a 340B discounted drug (either directly or through a contract pharmacy 106) to a person who is not a qualified patient 104b of the qualified entity 102b. Preventing diversion in a pharmacy 106 that disburses medications to both non-qualified patients 104a and qualified patients 104b can create a significant administrative burden.

One method of inventory control a pharmacy 106 may employ to comply with 340B regulations involves maintaining a separate physical inventory. Essentially the pharmacy 106 maintains a 340B inventory and a regular inventory. This method can require significant shelf space and substantially doubles the administrative overhead to maintain the inventory. Maintaining a separate inventory also presents challenges in tracking which inventory is 340B inventory and which inventory is not. Moreover, having separate 340B inventory creates a high risk of diversion, or distributing 340B medication to non-qualified patients 104a. When the regular inventory is depleted, the 340B medication could easily be sold to a non-qualified patient 104a, whether intentionally or unintentionally.

The replenishment model, another method of inventory control, is very effective in preventing diversion and double-dipping while also providing an option for reduced costs. In one implementation, the replenishment model enables a pharmacy 106 to manage their 340B inventory virtually while receiving 340B replacement medication on a replenishment basis. The replenishment model provides a form of inventory control that allows a pharmacy 106 to dispense medication to 340B covered patients 104 from its own inventory 110, and then have that inventory 110 replenished by the qualified entity 102b. In effect, the pharmacy 106 "loans" the qualified entity 102b the medication, and the qualified entity 102b then orders replacement inventory for the pharmacy 106. The present disclosure is directed to methods and systems for implementing a replenishment model of inventory control. Accordingly, more detailed explanation of replenishment generally, and two variations of replenishment, is provided in connection with FIGS. 3-11 below.

In addition to the challenges of coordinating bill-to/ship-to arrangements and avoiding double-dipping and diversion, other regulatory oversight and the sheer complexity of the regulations creates significant challenges to many general-service pharmacies that may seek to support the 340B program. The complexities of the programs and the regulations of the discount programs make computer programs and/or computer systems that facilitate participation in such discount programs desirable.

Computer programs and/or systems can be designed and implemented to provide the required functions in accordance with the regulations of one or more discount programs to enable pharmacies to participate in these discount programs. Typically a pharmacy 106 will have a computer or computer system 122 at the pharmacy 106. The pharmacy 106 may further have Coordination of Benefits (COB) software. The COB software may comprise a COB module running on the pharmacy computer system 122 or a separate COB system on a separate computer and or computer system. As used herein, a COB system 124 can be either a COB module and/or a COB system. A pharmacy 106 typically utilizes the COB system 124 when a patient is covered by two different insurance carriers. The COB system 124 can determine which insurance carrier pays which portion of an amount owed. The COB system 124 can coordinate a first adjudication of a prescription to a first payer (e.g., a first insurer) and a second adjudication of the prescription to a second payer (e.g., a second insurer). The COB system 124 may also be used to manage clinical programs, such as adherence and persistence programs.

In one embodiment, a computer program or system to facilitate participation in one or more discount programs can be designed to interface with the existing COB system. An interface with an existing COB system can be accomplished through a software API, a hardware API, an adaptation of the existing COB system, or a plug-in for the COB system. In another embodiment, a computer system may also be configured to implement a COB system as part of providing functions to enable participation in discount programs.

Many COB systems use an industry standard data format, such as the National Council for Prescription Drug Programs (NCPDP) standard. The COB data structures (e.g., the NCPDP compliant data structures) may be leveraged to support the qualified programs' process for pharmacy replenishment. In this way, a qualified entity may work with a pharmacy to leverage the pharmacy's existing COB systems and/or infrastructure to support highly-complex qualified programs and avoid the diversion and "double-dipping" regulatory pitfalls associated with such programs. Although the NCPDP standard is specifically mentioned herein, there are many variations of the COB system and data structures in the art, any of which may be modified and/or adapted for use in a replenishment pharmacy system. As such, this disclosure should not be read as limited to any particular COB data structure.

Restocking

Figure 2:
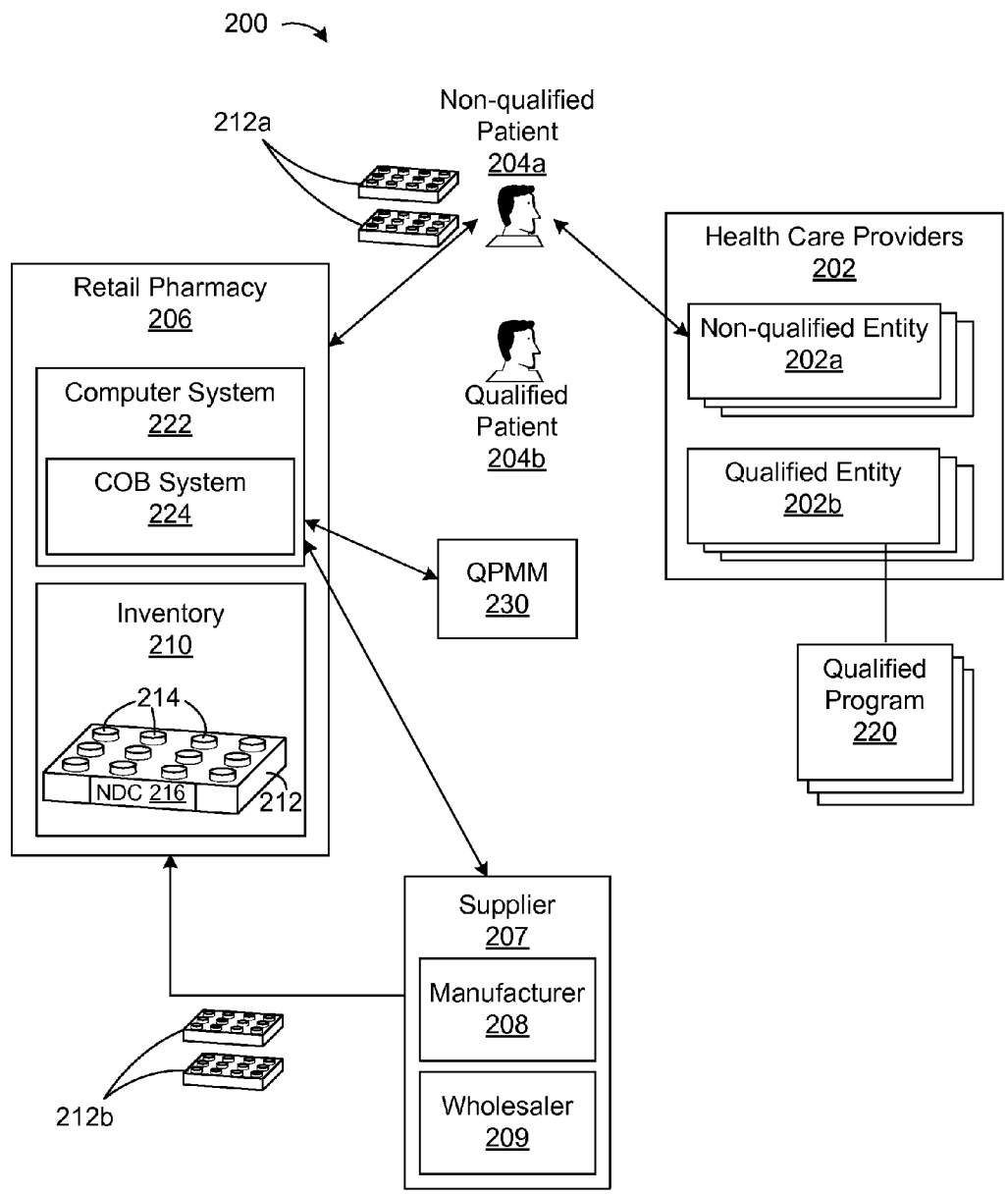
FIG. 2 is a block diagram of a one embodiment of a system for dispersal of medications through a pharmacy and for restocking and replenishment of disbursed inventory, the diagram depicting a restocking scenario.

FIG. 2 is a block diagram of one embodiment of a system 200 for dispersal of medications through a pharmacy 206. The system 200 allows for restocking and replenishment of disbursed inventory. The diagram depicted shows the interactions between participants in a restocking scenario. The pharmacy 206 disburses to patients 204 of health care providers 202. The health care providers 202 can include both non-qualified entities 202a and qualified entities 202b and the patients 204 can include both non-qualified patients 204a and qualified patients 204b. The qualified entities 202b can be qualified under, and participate in, one or more qualified programs 220.

In the simple restocking scenario of FIG. 2, the pharmacy 206 disburses medication 214 to only non-qualified patients 204a of health care providers 202. When the pharmacy inventory 210 for a medication 214 drops below a minimum threshold, or when a replacement threshold has been met, the pharmacy replaces the disbursed inventory 210 by placing a restocking order. The pharmacy 206 restocks inventory 210 for the medication 214 from suppliers 207, which can be pharmaceutical manufacturers 208 and wholesalers 209.

The pharmacy 206 can have a computer system 222 to facilitate various administrative functions of the pharmacy such as inventory management, transaction processing, and adjudication. Adjudication is the term for the procedure in which a pharmacy 206 determines the co-pay or other cost to be born by a patient 204, the process in which insurance coverage is requested on behalf of a patient 204 for purchased medication, and the determination of which insurance provider pays which portion of the amount due in cases where an insured has multiple insurers. As is well known in the art, the computer system 222 can comprise a processor (not shown), an output device (not shown) in electrical communication with the processor, and a memory (not shown) electrically coupled to the processor and output device. The memory may comprise an operating system and a plurality of applications and/or software modules. The computer system 222 may further include a COB system 224.

The computer system 222 can track medication disbursements. In one embodiment, barcode or like technology can be used to track disbursements. Each medication container 212 can include a barcode or other identifier, which is disposed on the container. The barcode or other identifier may include information as to the type of medication, the corresponding NDC 216, the amount of medication, the cost, etc. An optical scanner or other device used for scanning may be in electrical communication with the computer system 222 through any one of a number of conventional connections and/or networks, including but not limited to USB, PS2, and the Internet.

The computer system 222 can facilitate placement of a restocking order to replace disbursed inventory 210. The computer system 222 can track disbursements and manage minimum thresholds and/or replacement thresholds. When inventory 210 needs to be replaced, the computer system 222 can place an order with a supplier 207.

In the embodiment of FIG. 2, a qualified program management module (QPMM) 230 can extend the COB system 224 to facilitate participation of the pharmacy in one or more discount programs. The QPMM 230 can be configured to extend the functionality of the COB system 224 to administer the highly-regulated qualified programs. The QPMM 230 operates in parallel with the COB system 224 of the pharmacy 206. The QPMM 230 can track medication disbursements via the pharmacy computer system 222, including any barcode scanning equipment or other tracking system or technology. The QPMM 230 can perform inventory tracking and management functions and replenishment functions that may provide the additional benefit of reducing costs for the qualified entity 202b, pharmacy 206, and/or qualified patient 204b. Replenishment is discussed in greater detail below with reference to FIG. 3. If the pharmacy 206 is a contracted pharmacy operating under a replenishment model, after the qualified entity 202b provides the pharmacy 206 with replacement medication, the qualified entity 202b recoups from the pharmacy 206 any revenues generated for the medication minus dispensing and other service fees payable to the pharmacy 206. The larger the differential between the disbursement price of the medication and the replacement cost, the greater the savings for the qualified entity 202b. The QPMM 230 can coordinate recoupment of revenues, and may aid in increasing the differential to increase the savings for the qualified entity. The QPMM 230 can also be used to delay replenishment and/or restocking orders as needed. For example, a particular patient may require a very expensive medication. The pharmacy may only sell that medication to the one patient, and may not want to stock such an expensive medication until a few days before that patient is expected to re-fill the prescription. The QPMM 230 can facilitate coordinating the delayed replenishment and/or delayed restocking.

In another embodiment, a QPMM 230 can simply provide the functionality to administer the qualified programs, rather than extending the functionality of the COB system 224. The QPMM 230 can interface with the computer system 222 and/or the COB system 224. The QPMM 230 operates in parallel with the computer system 222 and/or the COB system 224 of the pharmacy 206. The QPMM 230 can track medication dispersals by gathering tracking information from the pharmacy computer system 206. The QPMM 230 is discussed in greater detail below with reference to FIGS. 3-11, with particular reference to FIGS. 4A, 4B, 7A, 7B, 10A and 10B.

In a restocking scenario, as depicted in FIG. 2, the pharmacy 206 may disburse two containers 212a of medication 214 to non-qualified patients 204a. The disbursement may meet or exceed a replacement threshold, such that the computer system 222 sends a replacement order to a supplier 207 requesting two replacement containers to restock the inventory 210. The pharmacy 206 pays the supplier for the order of replacement containers. Accordingly, the supplier sends two replacement containers 212b to the pharmacy 206. The replacement containers 212b are received, replacing the disbursed inventory 210 and restoring the inventory levels. The system 200 achieves the desired outcome in this scenario; the pharmacy inventory levels are restored to the same number of containers 212 as were on hand prior to disbursement of the two disbursed containers 212a. However, in a mixed disbursement scenario, involving disbursements to both non-qualified patients 204a and qualified patients 204b, a different outcome may result. The restocking procedures of the pharmacy and the replenishment procedures under a qualified plan may interfere and/or overlap. The overlap may cause inaccurate or improper replacement of disbursed medication in a manner that leads to an excess inventory situation as described below with reference to FIG. 3.

Replenishment

Figure 3:
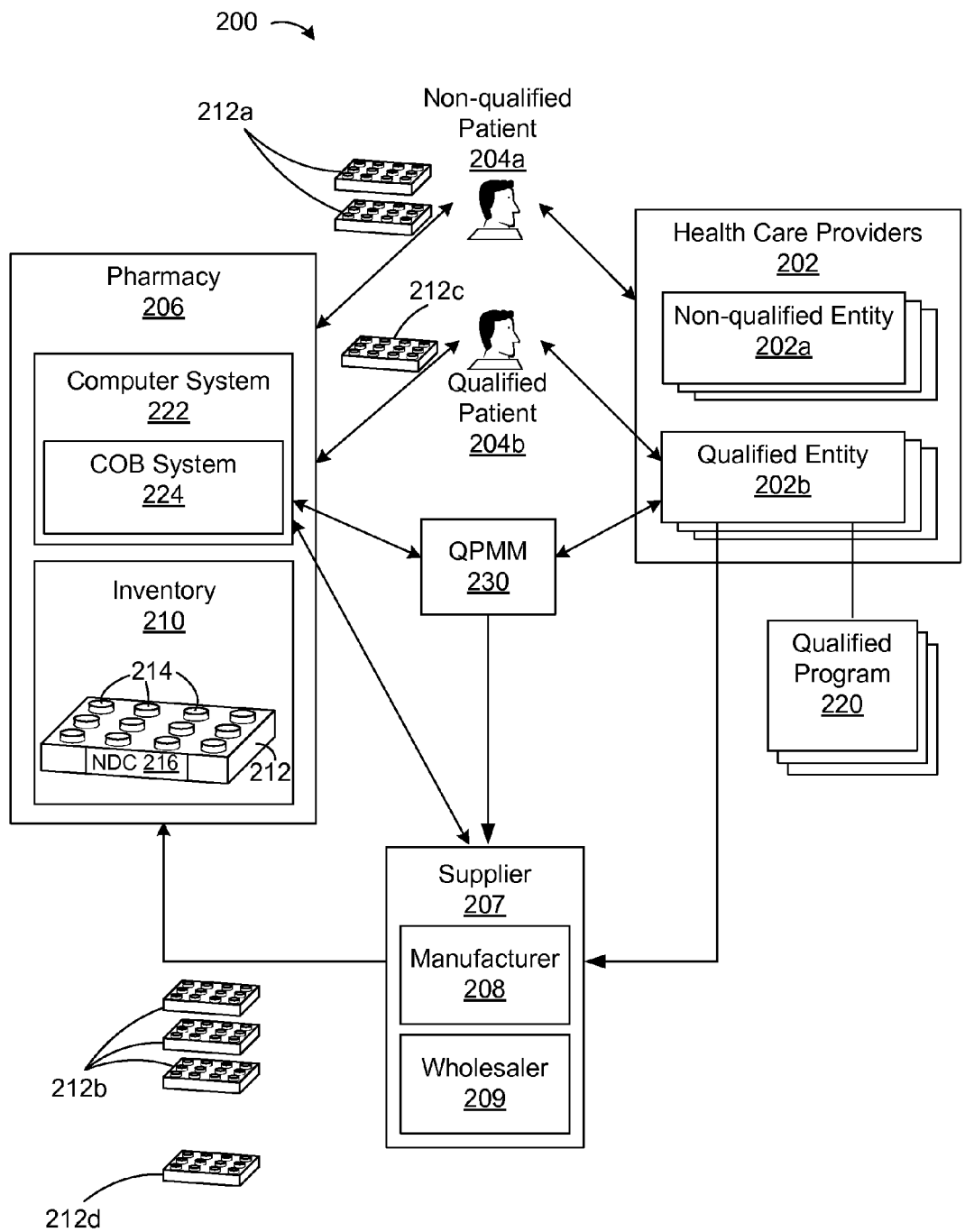
FIG. 3 is a block diagram of the system of FIG. 2 depicting traditional replenishment.

FIG. 3 is a block diagram of the system 200 of FIG. 2, the diagram showing the interactions between participants in a restocking and replenishment scenario. In the replenishment and restocking scenario of FIG. 3, one or more qualified entities 202b contract with a pharmacy 206 to disburse medications to their qualified patients 204b. The contracted pharmacy 206 may be a retail pharmacy. Although under contract with the one or more qualified entities 202b, the contract pharmacy 206 may disburse medication 214 to both non-qualified patients 204a and qualified patients 204b of a variety of health care providers 202 (both non-qualified entities 202a and qualified entities 202b). As before, when the pharmacy inventory 310 for a medication 314 drops below a minimum threshold, or when a replacement threshold has been met, the pharmacy 206 replaces the disbursed inventory 210 by placing a restocking order. The computer system 222 of the pharmacy 206 can facilitate placing the restocking order, as described above with reference to FIG. 2. In addition, when a replenishment threshold has been met, the QPMM 230 coordinates a replenishment order.

In one embodiment the QPMM 230 can comprise a software module running on a separate computer, as depicted in FIG. 3. The separate computer can be a separate computer at the pharmacy or managing service computer in network communication with one or more pharmacy computer systems. The QPMM 230 can be in electrical communication through a network with the pharmacy computer system 222 and/or computers of the health care providers (not shown). In another embodiment, the QPMM 230 can be a software module resident on the pharmacy computer system 222.

The QPMM 230 tracks the amount of dispensed medication and determines when the number of qualified disbursements reaches a replenishment threshold. In one embodiment, upon the number of qualified disbursements reaching the replenishment threshold, the QPMM 230 can coordinate replenishment by sending a replenishment order to a supplier 207 on behalf of a qualified entity 202b. The QPMM 230 can facilitate a "bill-to/ship-to" arrangement that enables a qualified entity 202b to make payment directly to the supplier 207, in compliance with the 340B program requirements or requirements of another qualified program 220, while replenishment containers are shipped directly to the contracted pharmacy 206. The supplier 207 can wait to send replenishment containers until payment is received, or immediately send the replenishment containers and await payment. On some occasions, the replenishment order and payment will be received by the supplier 207 nearly simultaneously.

As will be appreciated by a person of ordinary skill, the replenishment model may be complicated by the fact that various qualified programs 220 may have different regulations regarding how medications are replenished to the contracted pharmacy 206. For example, under 340B, replenishment medications 214 may be purchased by the qualified entity 202b and shipped directly from the manufacturer to the contracted pharmacy 206. Accordingly, the QPMM 230 may be configured to support a "bill-to/ship-to" directly from the supplier for shipment to the contracted pharmacy 206 with payment by the qualified entity 202b. However, other qualified programs may not allow for this type of transaction. As such, the QPMM 230 may be configured to perform the appropriate replenishment processes according to the appropriate qualified program 220. For example, in another embodiment, the QPMM 230 can also send to the qualified entity 202b payment instructions, or even a bill on behalf of the supplier 207. In still another embodiment, the QPMM 230 can coordinate an arrangement whereby the supplier 207 sends the requested replenishment containers to the contract pharmacy 206 and then the supplier 207 bills the paying qualified entity 202b.

In still another embodiment, the QPMM 230 can coordinate a replenishment order by notifying an operator through an output device (not shown). The output device may include a monitor or display running a suitable graphical user interface to thereby notify a user. Notifications can also be performed through a variety of other techniques including but not limited to email, updating a record in a database, a hardcopy print-out updating a spreadsheet, facsimile, telephone call, SMS text message, and the like.

The restocking and replenishment scenario, as depicted in FIG. 3, illustrates a challenge often encountered when a pharmacy 206 is replacing inventory disbursed to both non-qualified patients 204a and qualified patients 204b. In the scenario of FIG. 3, the pharmacy may disburse two containers 212a of medication 214 to non-qualified patients 204a and one container 212c of medication 214 to qualified patients 204b of qualified entities 202b. The total number of containers disbursed (in this case three) may exceed a replacement threshold. Accordingly, a typical computer system 222 at a pharmacy 206 sends a replacement order to a supplier 207 requesting three replacement containers to restock the inventory 210. The pharmacy 206 pays the supplier for the order of replacement containers. Accordingly, the supplier sends three replacement containers 212b to the pharmacy 206. The replacement containers 212b are received, the disbursed inventory 210 is replaced, restoring the inventory levels restored.

Meanwhile, the QPMM 230 is also monitoring disbursements of medication 214 by the pharmacy 206 and tracking qualified disbursements. As previously described, the QPMM 230 tracks the number of qualified disbursements until a replenishment threshold is met, at which point the QPMM 230 coordinates a replenishment order on behalf of one or more qualified entities 202b to request replenishment containers be sent to the pharmacy 206. If the replenishment threshold in the scenario of FIG. 3 is one container, the QPMM 230 will coordinate a replenishment order requesting that one replenishment container be sent to the pharmacy 206. Accordingly, the supplier sends an additional container 212d to the pharmacy 206.

The resulting outcome is different than desired because the pharmacy receives more replacement containers than are needed and an "excess inventory" situation results. A total of four replacement containers are sent to the pharmacy 206, three restocking containers and one replenishment container. The pharmacy 206 receives the four replacement containers, which is one container more than the inventory requirements of the pharmacy 206 and one more container than actually desired. The pharmacy 206 receives an extra container that was not needed and for which it has paid a wholesale price that is likely higher than a discount price under a qualified discount program. As is evident, this outcome is undesirable.

The pharmacy having excess inventory (a.k.a. inventory swell) is problematic for various reasons. The excess inventory consumes space. The pharmacy 206 may not have sufficient shelf space to properly store the additional replacement container 212d and/or the pharmacy may not timely sell the medication units 214 in the additional replacement container 212d before the end of the shelf life. The excess inventory can also go "stale" (i.e. expire). If the medication units 214 remain in inventory longer than the shelf life, then under various statutes and regulations the medication units expire and must be discarded. An excess inventory situation, in which the excess inventory exceeds the available shelf space and/or the shelf life of the medication 214, causes unnecessary and costly waste. These problems are exacerbated when a particular medication is ordered solely for a particular patient, and an excess inventory of that medication results.

The discrepancy between desired inventory level and actual inventory level after an excess inventory situation arises does not resolve itself without manual intervention. The computer system 222 of the pharmacy 206 will continue to restock inventory as the replacement threshold is met and the QPMM 230 will continue to coordinate replenish inventory to comply with the qualified discount programs 220. Manual intervention is necessary to stop the pharmacy computer system 222 from placing future restocking orders. Manual intervention can be a costly administrative burden.

The excess inventory situation results due to the desirability of interfacing with and/or extending functionality of an existing pharmacy computer system 222 and/or COB system 224, combined with the impracticability (or inability) of altering restocking functionality of the existing pharmacy computer system 222 and/or COB system 224. Accordingly, a system and method that simply and efficiently facilitates interfacing with and/or extending an existing pharmacy computer system 222 and/or COB system 224 is desirable. A system utilizing a system and/or method of cached replenishment, as described below with reference to FIG. 6 can alleviate the challenges just described.

Figure 4A:
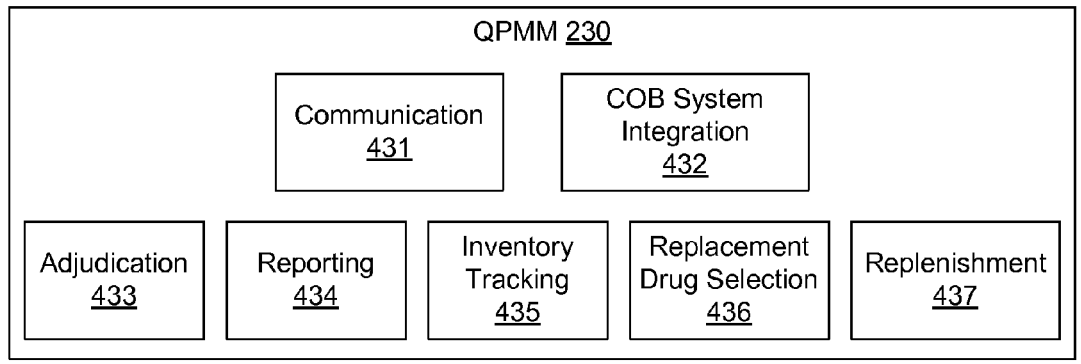
FIG. 4A is a block diagram of one embodiment of a Qualified Program Management Module (QPMM) that can enable a pharmacy to implement a traditional replenishment model.

FIG. 4A is a block diagram of one embodiment of a QPMM 230 that can enable a pharmacy to implement a traditional replenishment model. The QPMM 230 can comprise a communications module 431, a COB system integration module 432, an adjudication module 433, a reporting module 434, an inventory tracking module 435, a replacement drug selection module 436, and a replenishment module 437. The communications module 431 can enable the QPMM 230 to communicate with systems (e.g., computing devices and the like) of a pharmacy, a qualified entity, a supplier, and/or the like. The communications module 431 can also be configured to interact with a COB system of the pharmacy.

The COB system integration module 432 may be configured to extend the functionality of an existing COB system in the pharmacy. As discussed above, the COB system integration module 432 may extend and/or override one or more fields in one or more COB data structures to include information relating to a qualified entity and/or qualified program. The modified COB data structure may be used by the other components of the QPMM 230.

The adjudication module 433 can inject qualified program and/or qualified entity information into a COB data structure during the pharmacy's adjudication process (e.g., as medication is dispensed to a patient). In addition, the adjudication module 433 may interact with the inventory tracking module 435 and/or replenishment module 437 to determine whether an alternative NDC medication could be used to replenish the medication dispensed to the patient.

The reporting module 434 can process data in the COB data structure and generate reporting information per the requirements of the qualified programs and/or qualified entities served by the QPMM 230. As discussed above, qualified programs, such as 340B, GPO, and/or PAP programs may impose significant reporting requirements. These reporting requirements may be used to prevent abuse of the qualified programs (e.g., via diversion and/or double-dipping). The reporting module 434 may be configurable so that its operation may be modified responsive to changes in the requirements of the regulatory schemes governing qualified programs and/or qualified entities and/or the creation of new qualified programs and/or qualified entities.

The inventory tracking module 435 and/or the replenishment module 437 may track the inventory that the pharmacy "loans" to various qualified entities as the pharmacy dispenses medication to the patients of the qualified entities. The inventory tracking module 435 and/or the replenishment module 437 can track the number of medication units disbursed to qualified patients of qualified entities. The inventory tracking module 435 and/or the replenishment module 437 can determine when the number of qualified disbursements reaches a replenishment threshold. The inventory tracking module 435 may be configured to schedule replenishments of medications according to the dictates of the particular qualified program and/or qualified entity being serviced.

The replacement drug selection module 436 can monitor the discount pricing offered by suppliers under one or more qualified discount programs. The replacement drug selection module 436 can further determine a cost effective combination of containers by which to replenish inventory of the pharmacy. For example, a particular pharmacy may have corresponding replenishment threshold of one hundred medication units. A supplier may be offering a replenishment container of one hundred medication units for a discount program price of $25. A different supplier may be offering a replenishment container of fifty medication units for a discount program price of $10. The replacement drug selection module can determine that a more cost effective replenishment order would be to purchase two replenishment containers at $20 ($10 each), as compared to purchasing one replenishment container for $25. The replacement drug selection module 436 accordingly can configure the replenishment module 437 to coordinate replenishment orders through the supplier selling the containers of fifty for $10 and configure the replenishment module 437 to order the $10 containers.

The replenishment module 437 coordinates a replenishment transaction with a qualified entity, a pharmacy, and a supplier. As explained previously, the replenishment module 437 may track the inventory that the pharmacy "loans" to various qualified entities as the pharmacy dispenses medication to the patients of the qualified entities. The replenishment module 437 can track the number of medication units disbursed to qualified patients of qualified entities. The replenishment module 437 can determine when the number of qualified disbursements reaches a replenishment threshold. Once the replenishment threshold is reached, the replenishment module 437 can coordinate payments by one or more qualified entities and shipment to the pharmacy by a supplier. The replenishment module 437 can comprise a qualified entity interface module 438 and a supplier interface module 439, as discussed in greater detail below with reference to FIG. 4B.

A person having ordinary skill in the art will appreciate that a QPMM 230 can be configured a variety of ways, including combining and/or integrating one or more of the modules and/or functions described above. A QPMM 230 can also comprise additional modules to perform additional functions as necessary to enable compliance with requirements of one or more qualified discount programs. Furthermore, a QPMM 230 can also comprise fewer modules and functions than described above.

As can also be appreciated, the QPMM 230 runs on a computer comprising a processor and a memory, including any of the memory embodiments discussed above. The memory may include an operating system and a memory comprising the modules of the QPMM 230 as previously discussed.

The QPMM 230 may be in electrical communication with health care provider computers and a pharmacy computer 222 (depicted in FIG. 3) through a network. In one embodiment, upon reaching the replenishment threshold, the QPMM 230 may notify a user through an output device. The output device may include a monitor or display running a suitable graphical user interface to thereby notify a user. Notification may also be performed through a variety of other techniques including email, updating a record in a database, hardcopy print-out, updating a spreadsheet, and the like.

The QPMM 230 may be in electrical communication through a network, or another network, with a computer at a supplier. When a replenishment threshold corresponding to an NDC is reached, the QPMM 230 may notify the supplier computer and place an order for a replacement container. The replacement container typically comprises the same number of medication units. In this manner, disbursed medication units are replaced expeditiously.

The QPMM 230 may notify a health care provider computer of when a prescription is received at the participating pharmacy, when the prescription is filled, and the medication unit that is dispensed. A health care provider 202 is thereby informed of the status of prescriptions provided to its patients 204. If desired, the health care provider 202 may also be informed as to the replenishment of inventory 210 disbursed through qualified disbursements. As disclosed herein, the system 200 is able to ensure compliance with the 340B program.

The QPMM 230 may further maintain an account corresponding to the NDC and the individual health care providers. The account may include information regarding the dispersal of the medication units, a charge associated with the dispersal of each medication unit, orders for replacement containers corresponding to the NDC, and the charge associated with the dispersal of each replacement container. The QPMM 230 may determine each health care provider's share of cost for the replacement container. As can be appreciated, calculating share of cost may be determined in a variety of ways but typically is proportional to the number of medication units prescribed by each health care provider. The QPMM 230 may further generate an invoice for each health care provider 302 to convey the share of cost. The invoice may be communicated to each health care provider over the network.

Figure 4B:
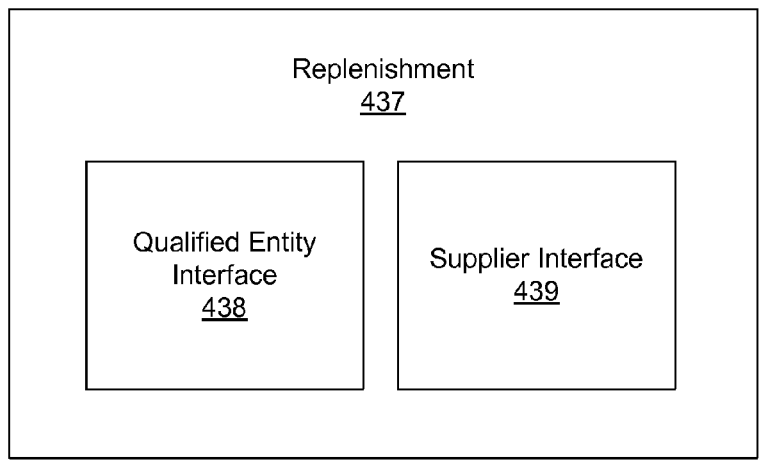
FIG. 4B is a block diagram of one embodiment of a replenishment module configured to implement a traditional replenishment model.

FIG. 4B is a block diagram of one embodiment of a replenishment module 437 configured to implement a traditional replenishment model. The replenishment module 437 can include a qualified entity interface module 438 and a supplier interface module 439. The qualified entity interface module 438 can coordinate payments from qualified entities to suppliers for replenishment orders. The qualified entity interface module 438 can be configured to coordinate such payments in a variety of prescribed methods as may be necessary to comply with the requirements of one or more qualified discount programs. Moreover, the qualified entity interface module 438 can be configured to coordinate payments from qualified entities in a variety of prescribed methods as may be necessary to interface with the protocols and methods of a variety of qualified entities, since these protocols and methods may vary from among qualified entities. For example, some qualified entities may receive electronic communications providing replenishment order information and payment instructions, whereas other qualified entities may require receipt of a hard copy document before payments will be processed.

The supplier interface module 439 can coordinate replenishment orders from suppliers. The supplier interface module 439 can be configured to place replenishment orders in a variety of prescribed methods as may be necessary to comply with the requirements of one or more qualified discount programs. Moreover, the supplier interface module 439 can be configured to place replenishment orders in a variety of methods as may be necessary to interface with the protocols and methods of a variety of suppliers, since these protocols and methods may vary among suppliers. For example, some suppliers may receive electronic communications that include a replenishment order, whereas other qualified entities may require receipt of a hard copy document before a replenishment order will be processed.

Figure 5:
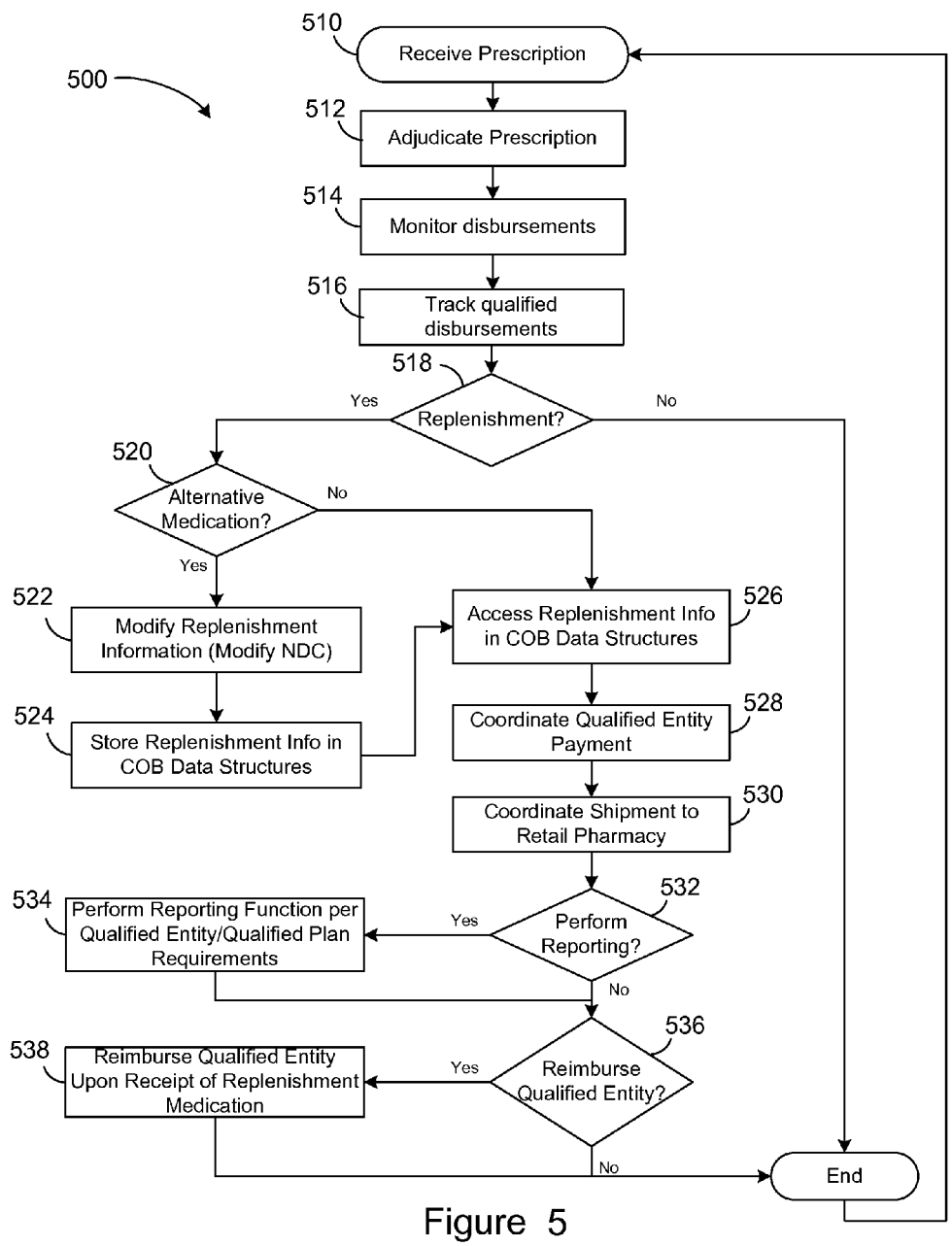
FIG. 5 is a flow chart of a method for replenishment of pharmaceuticals.

FIG. 5 is a flow diagram of one embodiment of a method 500 for replenishment of pharmaceuticals. A patient served and/or covered by a qualified entity may present a prescription to the pharmacy. The pharmacy receives 510 the prescription and begins processing the prescription. The pharmacy may adjudicate 512 the prescription. The adjudication may be accomplished by a computer system at the pharmacy. The computer system at the pharmacy may further comprise a COB system. The adjudication 512 may comprise providing the medication to the patient, determining the patient's portion of the cost of the medication (e.g., the co-pay), determining an insurer's portion of the cost, or the like.

During the adjudication 512, information relating to the adjudication may be gathered and stored in a COB data structure and/or COB system of the pharmacy. Such information may relate to the qualified entity that provides coverage and/or care to the patient, and/or the qualified program used by the qualified entity to obtain discounted medications. Information identifying the patient's qualified entity and/or qualified program may also be obtained and stored in a COB data structure. The qualified program-related information can be used to adjudicate the prescription transaction (e.g., determine the co-pay or other cost to be borne by the patient and/or the qualified entity covering the patient), to generate reporting information required by the qualified program, to perform inventory management, and manage payment in accordance with policies and procedures of the qualified program.

Disbursements of medication are monitored 514. A QPMM can monitor the disbursements of medication to qualified and/or non-qualified patients. Monitoring can occur by interfacing with the computer system at the pharmacy and/or the COB system on the computer system. Interfacing with the COB system can be accomplished directly and/or by accessing one or more COB data structures. When monitoring the disbursements, the number of qualified disbursements can be tracked 516. When a qualified disbursement occurs, the method 500 can determine 518 whether replenishment is needed. Replenishment under a given qualified plan may be dictated by the regulations of the qualified program and/or qualified entity; replenishment may be required after a certain amount of medication has been "loaned" to the qualified entity by the pharmacy and/or the inventory of the medication loaned by the pharmacy has been depleted to a threshold level. The method can determine whether the number of qualified disbursements has reached or exceeded a replenishment threshold. If replenishment is not needed, then the method can end.

If the method 500 determines that replenishment is needed, the method may determine 520 whether a lower cost alternative medication is available in place of the medication dispensed to the patient at step 512. As discussed above, in some cases, an equivalent medication may be available from an alternative supplier (e.g., manufacturer or wholesaler) for a lower price. Available equivalent medications may be identified using the NDC of the medication dispensed at step 512. The medication may be equivalent, or even identical, and simply the quantity in the container may be different. The nature of the qualified entity and/or the qualified program may determine whether a particular discounted medication is available. If an acceptable lower-cost alternative is found, the new replenishment information, including the alternative NDC and supplier information, may be recorded 522. The recorded information can also be stored 524 in a COB data structure. The stored information can include information relating to the qualified entity, qualified program, and/or alternative replenishment NDC.

Method 500 may use the replenishment information that is accessed, whether original information or new information, to coordinate the payment and shipping functions of replenishment and to replenish the medication according to the regulations of the particular qualified program and/or qualified entity identified in the COB data structure. If a "bill-to/ship-to" arrangement is allowed by the qualified program and/or qualified entity, the method 500 may dispatch an order for replenishment medication to a supplier to be shipped to the pharmacy. The billing for the order may be sent to the qualified entity. As discussed above, in some cases the medication may be replenished from a different supplier to take advantage of periodic discounts available to the qualified entity and/or qualified program.

The replenishment information that is accessed 526 by the method 500 can include, but is not limited to, information about the qualified entity, the qualified plan, the NDC, and the supplier. The replenishment information is used to coordinate replenishment. The replenishment information can be accessed 526 from the COB data structure. In an alternative embodiment, the replenishment information can be accessed from data in the memory of the pharmacy computer system and/or COB system.

The replenishment information that is accessed 526 can be used by the method 500 to coordinate 528 payment for the replenishment order by the qualified entity. The replenishment information can include, but is not limited to, contact information for the qualified entity, preferred and/or accepted forms of communication with the qualified entity, and protocols and procedures followed by (or for interfacing with) the qualified entity. The replenishment information can further include pricing and quantity information, as well as qualified plan information. Coordination of payment may include electronic communication and/or hard copy communication to the qualified entity. The communication can outline instructions and terms for payment to the supplier. In another embodiment, the communication to the qualified entity can be an invoice sent on behalf of the supplier containing information regarding the shipment of the replenishment order. In another embodiment, coordination of payment may comprise providing the supplier with information as to how to directly bill the qualified entity for a replenishment shipment to a pharmacy.

The replenishment information can also be used by the method 500 to coordinate 530 shipment of the replenishment medication to the pharmacy. The replenishment information can include, but is not limited to contact information for the supplier, protocols and forms of communication accepted by the supplier, the pharmacy shipping address, preferred and/or accepted forms of shipment, preferred and/or accepted forms of communication with the pharmacy, protocols and procedures for interfacing with the pharmacy, and quantity and packaging information. Coordination of shipment of replenishment medication may include electronic communication and/or hard copy communication to a supplier providing shipping instructions. In another embodiment, the communication to the supplier can include instructions and information for the supplier to directly bill the qualified entity for a replenishment shipment.

After payment and shipment are coordinated, the method 500 can determine 532 whether reporting is necessary and/or appropriate under the qualified discount plan under which the medications were disbursed. The nature and timing of the reporting may vary depending on the particular qualified program and/or qualified entity serviced by method 500. If reporting is required, the method 500 can perform reporting 534 according to the requirements of the applicable qualified discount plan. If no reporting is necessary, the flow of the method 500 can continue. Performing reporting may further comprise accessing the pharmacy COB data, and filtering the data to extract any data relating to a particular qualified program and/or qualified entity. The filtered data may be used to generate one or more reports for the pharmacy, qualified entity, and/or qualified program. The reporting data may indicate the amount and nature of medication distributed to qualified entity patients, any replenishment actions taken, and the like. In alternative embodiments, access and filtering may be performed on a continual basis (e.g., as prescriptions are adjudicated), regardless of reporting.

The method 500 can also determine 536 whether the qualified provider should be reimbursed by the pharmacy for the difference between the disbursement price of the medication and the replenishment cost paid (minus any overhead and service fees charged by the pharmacy). Of course, the reimbursement 536 may be omitted if the replenishment coordination at steps 528 and 530 does not require reimbursement and/or reimbursement is prohibited by the qualified program and/or qualified entity.

A QPMM interfacing with a computer system and/or a COB system at the pharmacy can perform much, or all, of the method. The QPMM can monitor 514 disbursements of medication, track 516 qualified disbursements, determine 518 whether replenishment is needed, and/or access 526 replenishment information to coordinate completion of replenishment. The QPMM can coordinate completion of replenishment by coordinating payment 528, coordinating shipment 530, performing reporting 534, and/or reimbursing a qualified entity 538. The QPMM can also, where possible, identify 520 any alternative replenishment medication, and modify 522 and store 524 new replenishment information for the identified alternative medication.

Cached Replenishment

As explained previously, traditional replenishment can result in an excess inventory situation when a pharmacy is disbursing medication to both qualified patients and non-qualified patients. As previously explained, an excess inventory situation can arise when an existing computer system of a pharmacy places restocking orders for all disbursed inventory, while at the same time a QPMM coordinates replenishment orders for the medications disbursed under a qualified discount plan. The creation of an excess inventory situation is undesirable because of the administrative burden and/or potential for wasted time and resources. Moreover, creating software to modify functioning of an existing pharmacy computer system and/or COB system is challenging due to variations among existing systems and/or COB modules. Accordingly, a system and method that simply and efficiently facilitates interfacing with and/or extending an existing pharmacy computer system and/or COB system is desirable. A system utilizing a system and/or method of cached replenishment can reduce or even eliminate excess inventory situations and can enable simple and efficient interfacing with and/or extension of the functionality of an existing pharmacy computer system.

Figure 6:
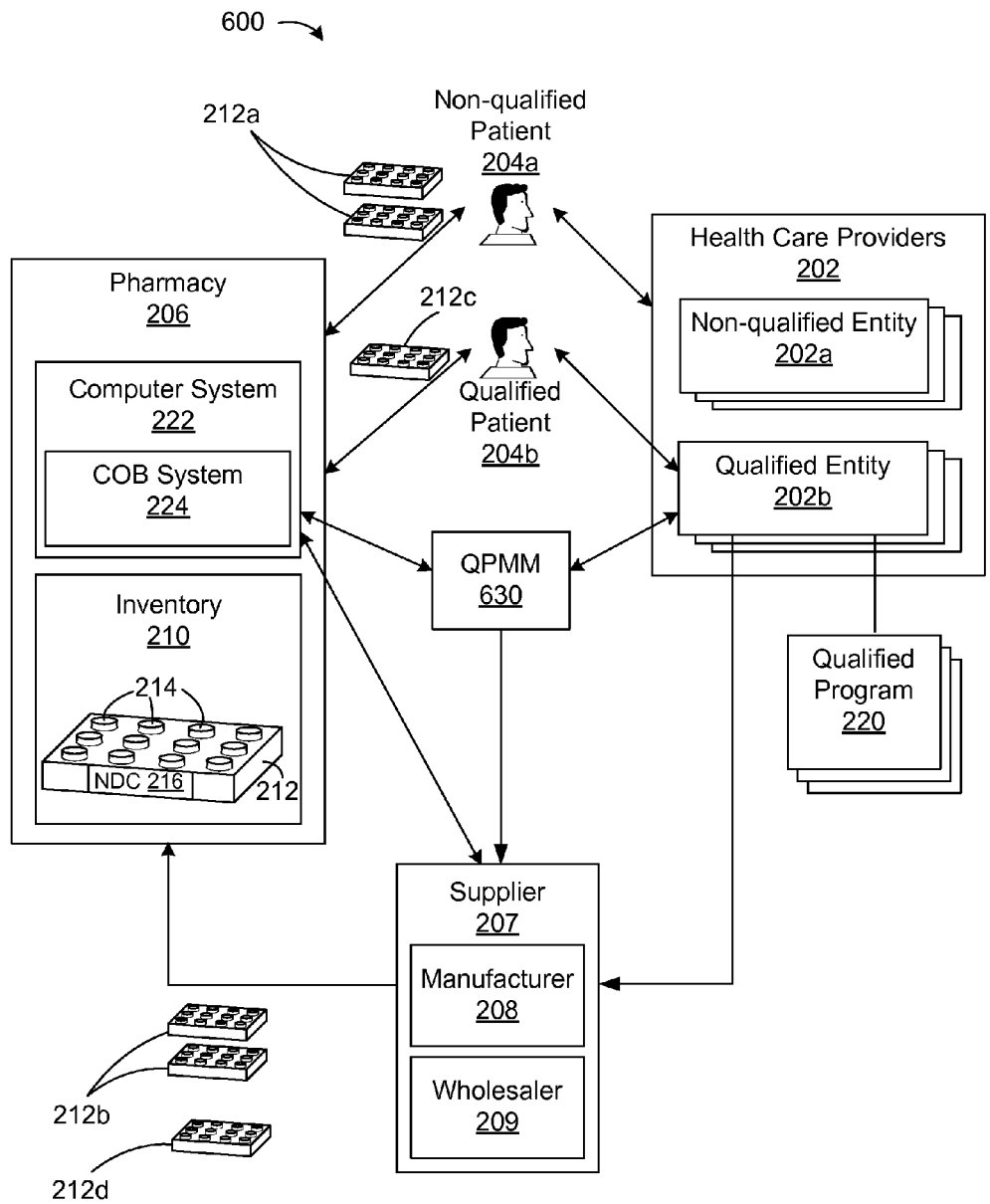
FIG. 6 is a block diagram of a system for dispersal of medications through a pharmacy and for restocking and cached replenishment of disbursed inventory, the diagram depicting cached replenishment.

FIG. 6 is a block diagram of another embodiment of a system 600 for dispersal of medications through a pharmacy 206. The system 600 enables restocking and cached replenishment of disbursed inventory. The diagram depicts the interactions between participants in a restocking and a cached replenishment scenario. The system 600 comprises a QPMM 630 that includes a system and/or method of cached replenishment. As before, the pharmacy 206 disburses to patients 204 of health care providers 202. The health care providers 202 can include both non-qualified entities 202a and qualified entities 202b and the patients 204 can include both non-qualified patients 204a and qualified patients 204b. The qualified entities 202b can be qualified under, and participate in, one or more qualified programs 220.

In a cached replenishment and restocking scenario, as depicted in FIG. 6, the pharmacy 206 disburses medication 214 to both non-qualified patients 204a and qualified patients 204b of health care providers 202, similar to the scenario of FIG. 3. As before, when the pharmacy inventory 210 for a medication 214 drops below a minimum threshold, or when a replacement threshold has been met, the pharmacy 206 replaces the disbursed inventory 210 by placing a restocking order. The computer system 222 of the pharmacy 206 can facilitate placing the restocking order. In addition, when a replenishment threshold has been met, the QPMM 630 can coordinate a cached replenishment order.

The QPMM 630 can be in electrical communication through a network with the pharmacy computer system 222 and/or computers of the health care providers (not shown). The QPMM 630 tracks the amount of dispensed medication and determines when the number of qualified disbursements reaches a replenishment threshold. Upon the number of qualified dispersals reaching the replenishment threshold, the QPMM 630 coordinates a cached replenishment order by sending a cached replenishment order to a supplier 207.

The cached replenishment order generates a replenishment purchase, but delays shipment of the ordered replenishment medication until the pharmacy places a restocking order with the supplier. The qualified entity 202b pays the supplier 207 the price of the replenishment container under the qualified discount program. However, rather than the supplier 207 shipping the replenishment container immediately, the supplier 207 holds shipment of the replenishment container until a restocking order is received from the pharmacy 206. The replenishment purchase is a purchase of a cached replenishment container. Accordingly the supplier 207 may reserve, or set aside, for the pharmacy 206 a container 212 of medication 214. The manufacturer may virtually set aside the cached replenishment container 212. In another embodiment, the manufacturer may physically set aside the cached replenishment container 212. When a restocking order is received by the supplier 207 from the pharmacy 206, the total number of restocking containers ordered is reduced by the number of cached replenishment containers reserved to the pharmacy 206. Then the remaining number of restocking containers and the cached replenishment containers are all shipped to the pharmacy 206.

As portrayed in FIG. 6, the pharmacy 206 may disburse one container 212c of medication units 214 to a qualified patient 204b. The QPMM 630 monitors the disbursements of medication units 214 by the pharmacy 206 and tracks the number of qualified disbursements. When the number of qualified disbursements reaches a replenishment threshold the QPMM 630 coordinates a cached replenishment order on behalf of one or more qualified entities 202b to purchase a cached replenishment container for the pharmacy 206.

If the replenishment threshold in the scenario of FIG. 6 is one container, the QPMM 630 will coordinate a cached replenishment order requesting a cached replenishment container and delayed shipment to the pharmacy 206. The one or more qualified entities 202b pay the discount price under the appropriate qualified discount program 220 for the cached replenishment container. The supplier 207 receives the cached replenishment order and receives payment from the qualified entities 202b. A cached replenishment container is reserved for the pharmacy. The supplier 207 does not ship any replenishment containers until a restocking order is received from the pharmacy 206.

Subsequently, in the scenario of FIG. 6, the pharmacy 206 may disburse two containers 212a of medication 214 to non-qualified patients 204a. The total number of containers 212 disbursed, three in this case, may also exceed a replacement threshold, or reduce the pharmacy inventory 210 for the medication 214 below a minimum threshold. When this happens, typically a computer system 222 at a pharmacy 206 sends a replacement order to a supplier 207 requesting three replacement containers to restock the inventory 210. A pharmacy computer system 222 typically does not track qualified disbursements separately from regular disbursements, as described above. Accordingly, the computer system 222 seeks to replace all disbursed inventory, and thus orders three containers, the total number of containers disbursed by the pharmacy 206.

The supplier 207 receives the restocking order from the pharmacy 206 and recognizes the cached replenishment container reserved for the pharmacy 206. Accordingly, one replacement container is subtracted from the total number of containers ordered in the restocking order, reducing the restocking order to two containers. The supplier 207 sends the pharmacy 206 a bill for two replacement containers and the pharmacy 206 pays the supplier 207 for only the two containers. The supplier 207 then sends the pharmacy 206 two restocking containers 212b for the restocking order and one cached replenishment container 212d. A total of three replacement containers are sent from the supplier. The replacement containers 212bd are received, the disbursed inventory 210 is replaced and the inventory levels are restored.

The desired outcome is achieved under the cached replenishment scenario. The pharmacy 206 disbursed three total containers (two to non-qualified patients 212a and one to qualified patients 212b), and received three replacement containers. The pharmacy 206 pays the wholesale price for replacement containers for medication disbursed to non-qualified patients and the qualified program discount price for replacement containers for medication disbursed to qualified patients. Moreover, an excess inventory situation is avoided. Finally, the result is accomplished without modification to the normal functioning of a computer system 222, or a COB system 224 running thereon, that is already in use at a pharmacy 206.

As can be appreciated, coordinating delayed shipment of a cached replenishment container can be accomplished a variety of ways. For example, a physical container 212 may be purchased on behalf of the pharmacy. Shipment of this container ("cached replenishment container") however, is delayed until a restocking order is received from the pharmacy. The supplier 207 reserves, or sets aside, a cached replenishment container 212 until a restocking order is received for that medication 214. When the restocking order is received, the supplier subtracts the total number of containers 212 ordered by the total number of replenishment containers 212 reserved, or set aside, for the pharmacy 206. The cached replenishment containers are then sent to the pharmacy along with any additional replacement containers.

In another embodiment, a computer system at the supplier may track a cached replenishment container as a special type of credit. The computer system creates (or indicates to the supplier to create) a cached replenishment credit to the pharmacy 206. The cached replenishment credit is for a replenishment container of medication credited to the pharmacy 206. Rather than crediting a dollar amount, the cached replenishment credit is for a replenishment container.

The QPMM 630 can coordinate a cached replenishment with a supplier 207 in a variety of ways. The QPMM 630 can generate a hardcopy (e.g. paper) cached replenishment request that is sent to the supplier 207. In another embodiment, the QPMM 630 generates an electronic request that is communicated to a computer system (not shown) of a supplier 207. The computer system of the supplier 207 can process the electronic request automatically. In still another embodiment, the QPMM 630 has permission to access a database of the supplier 207, and the QPMM 630 can generate a delayed shipment of a cached replenishment container to a pharmacy by directly manipulating data in the supplier database. In still another embodiment, the QPMM 630 can coordinate a cached replenishment order by notifying an operator through an output device (not shown). The output device may include a monitor or display running a suitable graphical user interface to thereby notify a user. Notifications can also be performed through a variety of other techniques including but not limited to email, updating a record in a database, a hardcopy print-out updating a spreadsheet, facsimile, telephone call, SMS text message, and the like.

The QPMM 630 can coordinate a cached replenishment with a qualified entity 202b in much the same way as coordinating a typical replenishment. The QPMM 630 can send payment instructions to the qualified entity 202b. In still another embodiment, the QPMM 630 can coordinate a cached replenishment entirely through a qualified entity 202b by providing the qualified entity 202b with payment instructions, as well as information to send with payment to the supplier 207 to request delayed shipment of a cached replenishment container to the appropriate pharmacy 206 in exchange for the payment.

Figure 7A:
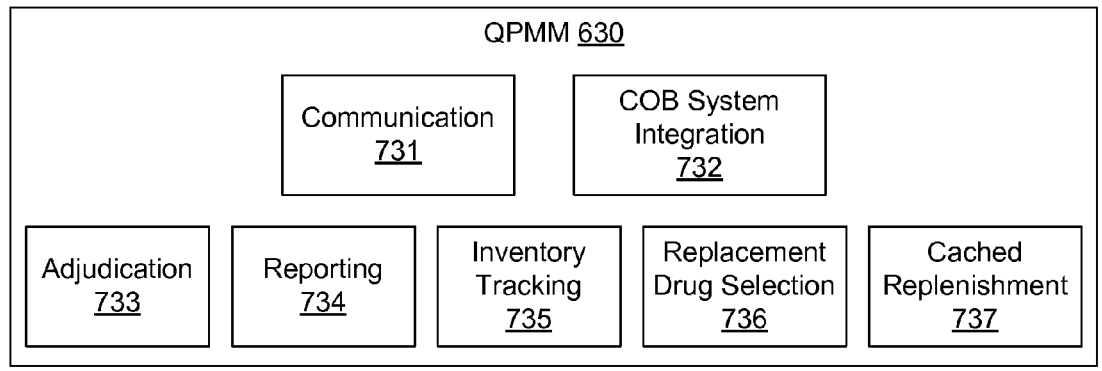
FIG. 7A is a block diagram of an embodiment of a QPMM that can enable a pharmacy to implement a cached replenishment model.

FIG. 7A is a block diagram of one embodiment of a QPMM 630 that can enable a pharmacy to implement a cached replenishment model. The QPMM 630 can comprise a communications module 731, a COB system integration module 732, an adjudication module 733, a reporting module 734, an inventory tracking module 735, a replacement drug selection module 736, and a cached replenishment module 737. The communications module 731, the COB system integration module 732, the adjudication module 733, the reporting module 734, the inventory tracking module 735, and the replacement drug selection module 736 can each operate similar to the corresponding modules of the QPMM 230 as described above with reference to FIG. 4A. The cached replenishment module 737 enables implementation of a cached replenishment model.

The cached replenishment module 737 coordinates a cached replenishment transaction with a qualified entity, a pharmacy, and a supplier. The cached replenishment module 737 may track the inventory that the pharmacy "loans" to various qualified entities as the pharmacy dispenses medication to the patients of the qualified entities. Described differently, the cached replenishment module 737 can track the number of medication units disbursed to qualified patients of qualified entities. The cached replenishment module 737 can also determine when the number of qualified disbursements reaches a replenishment threshold. In another embodiment, the cached replenishment module gathers and/or receives disbursement monitoring and tracking information from the communications module 731 and/or the inventory tracking module 735.

Once the replenishment threshold is reached, the cached replenishment module 737 can coordinate a cached replenishment by coordinating payments by one or more qualified entities to a supplier to purchase a delayed shipment of a cached replenishment to the pharmacy. The supplier recognizes and reserves a cached replenishment container for the pharmacy and delays shipment of the container to the pharmacy until a restocking order is received. When a restocking order for the medication is received from the pharmacy, the replenishment container is shipped to the pharmacy. The supplier can deduct the number of cached replenishment containers from the total number of containers of medication ordered by the pharmacy and ship the remaining number of containers as restocking containers. The supplier can then bill the pharmacy for only the number of restocking containers shipped. Accordingly, the total number of containers shipped is equal to the total number of containers disbursed and the pharmacy is billed for only the restocking containers, and not for the replenishment containers. In this manner, an excess inventory situation is avoided and a desired result is achieved.

In another embodiment, the cached replenishment module coordinates a cached replenishment by coordinating generation of a cached replenishment credit. The cached replenishment credit can be a special type of credit for a replenishment container rather than for a paid amount. Accordingly, the supplier will offset a future restocking order by a container rather than by a paid dollar amount. In still another embodiment an actual physical container is purchased on behalf of the pharmacy and set aside.

Figure 7B:
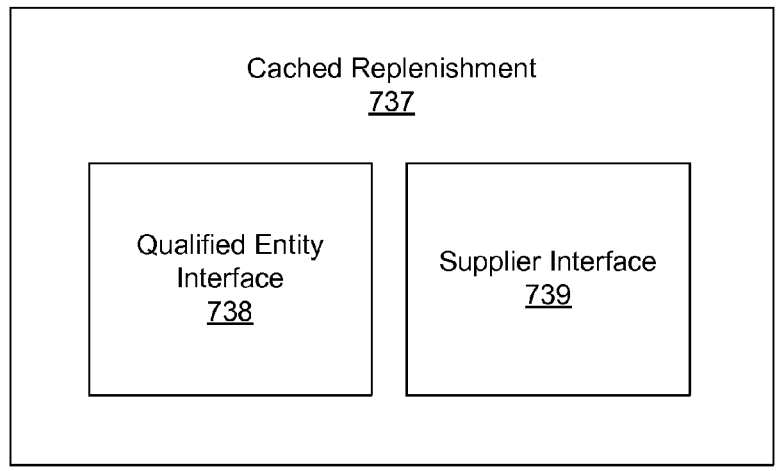
FIG. 7B is a block diagram of one embodiment of a cached replenishment module configured to implement a cached replenishment model.

FIG. 7B is a block diagram of one embodiment of a replenishment module 737 configured to implement a cached replenishment model. The cached replenishment module 737 can include a qualified entity interface module 738 and a supplier interface module 739. The qualified entity interface module 738 can coordinate payments from qualified entities to suppliers for replenishment orders. The qualified entity interface module 738 can be configured to coordinate such payments in a variety of prescribed methods as may be necessary to comply with the requirements of one or more qualified discount programs. Moreover, the qualified entity interface module 738 can be configured to coordinate payments in a variety of methods as may be necessary to interface with the protocols and methods of a variety of qualified entities, since these protocols and methods may vary from among qualified entities. For example, some qualified entities may receive electronic communications providing cached replenishment order information and payment instructions, whereas other qualified entities may require receipt of a hard copy document before payments will be processed.

The supplier interface module 739 can coordinate cached replenishment orders with suppliers. The supplier interface module 739 can be configured to place cached replenishment orders in a variety of prescribed methods as may be necessary to comply with the requirements of one or more qualified discount programs. Moreover, the supplier interface module 739 can be configured to place cached replenishment orders in a variety of methods as may be necessary to interface with the protocols and methods of a variety of suppliers, since these protocols and methods may vary from among suppliers. For example, some suppliers may receive electronic communications that include a cached replenishment order, whereas other qualified entities may require receipt of a hard copy document before a cached replenishment order will be processed. Still other suppliers may allow a QPMM to directly access the a computer system and/or database at the supplier. The QPMM can manipulate the data in the computer system and/or database at the supplier to reflect a cached replenishment credit.

Figure 8:
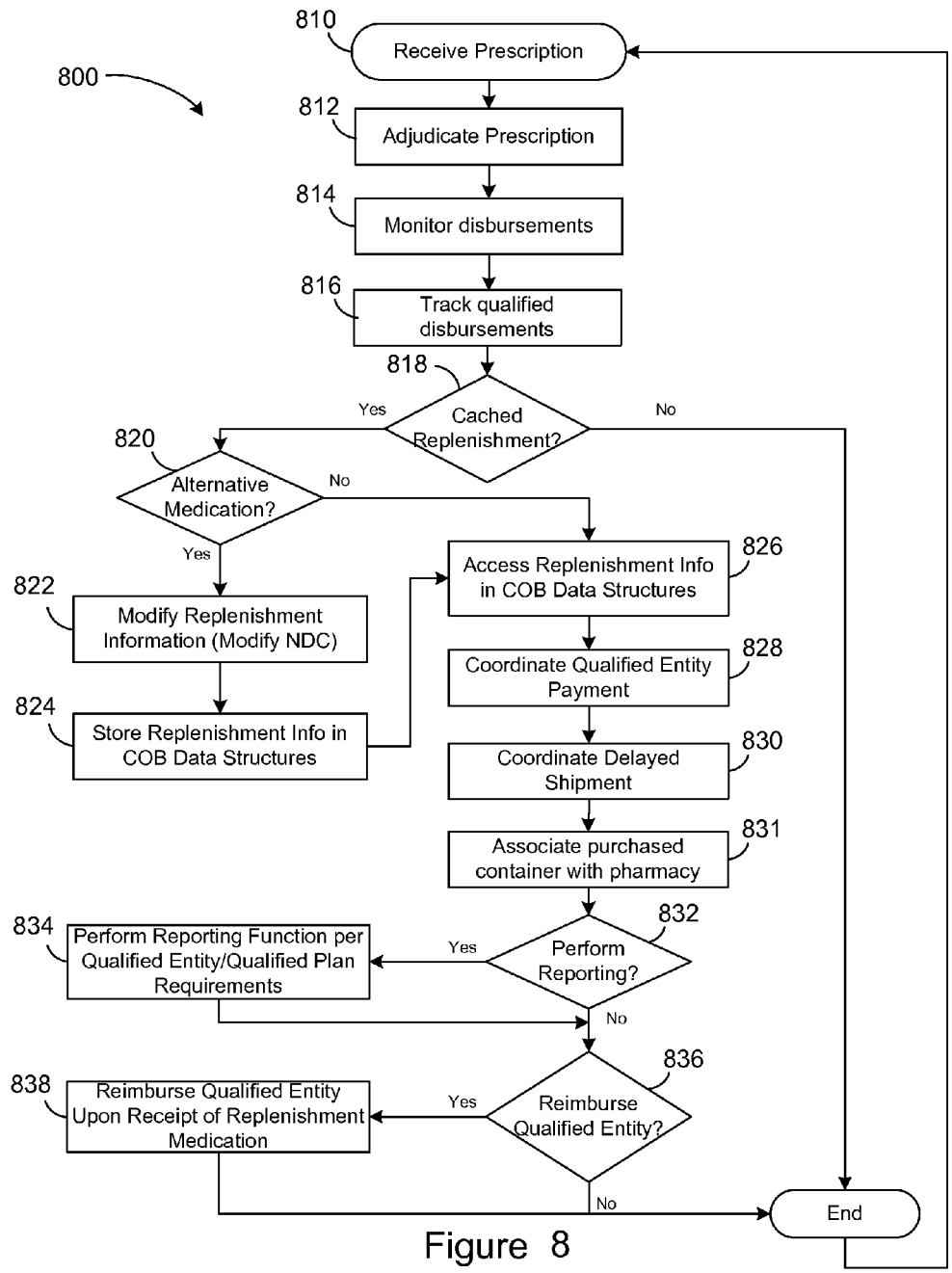
FIG. 8 is a flow chart of a method for cached replenishment of pharmaceuticals.

FIG. 8 is a flow diagram of one embodiment of a method 800 for cached replenishment of pharmaceuticals. A patient served and/or covered by a qualified entity may present a prescription to the pharmacy. The pharmacy receives 810 the prescription and begins processing the prescription. The pharmacy may adjudicate 812 the prescription. The adjudication may be accomplished by a computer system at the pharmacy. The computer system at the pharmacy may further comprise a COB system. The adjudication 812 may comprise providing the medication to the patient, determining the patient's portion of the cost of the medication (e.g., the copay), determining an insurer's portion of the cost, or the like. During the adjudication 812, information relating to the adjudication may be gathered and stored in a COB data structure and/or COB system of the pharmacy. Such information may relate to the qualified entity that provides coverage and/or care to the patient, and/or the qualified program used by the qualified entity to obtain discounted medications. Information identifying the patient's qualified entity and/or qualified program may also be obtained and stored in a COB data structure.

Disbursements of medication are monitored 814. A QPMM can monitor the disbursements of medication to qualified and/or non-qualified patients. Monitoring can occur by interfacing with the computer system at the pharmacy and/or the COB system. Interfacing with the COB system can be accomplished directly and/or by accessing one or more COB data structures. When monitoring the disbursements, the number of qualified disbursements can be tracked 816. When a qualified disbursement occurs, the method 800 can determine 818 whether a replenishment is needed. Replenishment under a given qualified plan may be dictated by the regulations of the qualified program and/or qualified entity; replenishment may be required after a certain amount of medication has been "loaned" to the qualified entity by the pharmacy and/or the inventory of the medication loaned by the pharmacy has been depleted to a threshold level. The method can determine whether the number of qualified disbursements has reached or exceeded a replenishment threshold. If replenishment is not needed, then the method can end.

If the method 800 determines that replenishment is needed, the method may optionally determine 820 whether a lower cost alternative medication is available in place of the medication dispensed to the patient at step 812. As discussed above, in some cases, an equivalent medication may be available from an alternative supplier (e.g., manufacturer or wholesaler) for a lower price. Available equivalent medications may be identified using the NDC of the medication dispensed at step 812. The medication may be equivalent, or even identical, and simply the quantity in the container may be different. The nature of the qualified entity and/or the qualified program may determine whether a particular discounted medication is available. If an acceptable lower-cost alternative is found, the new replenishment information, including the alternative NDC and supplier information, may be recorded 822. The recorded information can also be stored 824 in a COB data structure. The stored information may be stored in the pharmacy's COB system and can include information relating to the qualified entity, qualified program, and/or alternative replenishment NDC.

Method 800 may use the replenishment information that is accessed, whether original information or new information, to coordinate cached replenishment within the requirements and regulations of the particular qualified program and/or qualified entity identified in the COB data structure. The replenishment information can include, but is not limited to, information about the qualified entity, the qualified plan, the NDC, and the supplier. The replenishment information is used to coordinate cached replenishment, including purchase of a cached replenishment container and delayed shipment of such container to the pharmacy. The replenishment information can be accessed 826 from the COB data structure. In an alternative embodiment, the replenishment information can be accessed 826 from data in the memory of the pharmacy computer system and/or COB system.

The replenishment information can be used by the method 800 to coordinate 828 payment for the cached replenishment order by the qualified entity. The replenishment information can include, but is not limited to, contact information for the qualified entity, preferred and/or accepted forms of communication with the qualified entity, and protocols and procedures followed by (or for interfacing with) the qualified entity. The replenishment information can further include pricing and quantity information, as well as qualified plan information. Coordination of payment may include electronic communication and/or hard copy communication to the qualified entity. The communication can outline instructions and terms for payment to the supplier. In another embodiment, the communication to the qualified entity can be an invoice sent on behalf of the supplier containing information regarding the shipment of the replenishment order. In another embodiment, coordination of payment may comprise providing the supplier with information as to how to directly bill the qualified entity for a replenishment shipment to a pharmacy.

The replenishment information can also be used by the method 800 to coordinate 830 delayed shipment of the replenishment container to the pharmacy. The shipment from the supplier to the pharmacy is delayed until such time as the pharmacy places a restocking order with the supplier for the same medication. As can be appreciated, the delayed shipping can be accomplished in a variety of ways, including but not limited to a request to hold shipment, instructions regarding delay of shipment, instructions to delay filling the cached replenishment order, generation of a special type of credit for a cached replenishment container, and reserving a physical container for later shipment.

The replenishment information can include, but is not limited to contact information for the supplier, protocols and forms of communication accepted by the supplier, the pharmacy shipping address, preferred and/or accepted forms of shipment, preferred and/or accepted forms of communication with the pharmacy, protocols and procedures for interfacing with the pharmacy, and quantity and packaging information. Coordination of shipment of replenishment medication may include electronic communication and/or hard copy communication to a supplier providing shipping instructions. In another embodiment, the communication to the supplier can include instructions and information for the supplier to directly bill the qualified entity for a replenishment shipment.

After payment and delayed shipment are coordinated, the method 800 can determine 832 whether reporting is necessary and/or appropriate under the qualified discount plan under which the medications were disbursed. The nature and timing of the reporting may vary depending on the particular qualified program and/or qualified entity serviced by the method 800. If reporting is required, the method 800 can perform reporting 834 according to the requirements of the applicable qualified discount plan. If no reporting is necessary, the flow of the method 800 can continue. Performing reporting may further comprise accessing the pharmacy COB data, and filtering the data to extract any data relating to a particular qualified program and/or qualified entity. The filtered data may be used to generate one or more reports for the pharmacy, qualified entity, and/or qualified program. The reporting data may indicate the amount and nature of medication distributed to qualified entity patients, any replenishment actions taken, and the like. In alternative embodiments, access and filtering may be performed on a continual basis (e.g., as prescriptions are adjudicated), regardless of reporting.

The method 800 can also optionally determine 836 whether the qualified provider should be reimbursed by the pharmacy for the difference between the disbursement price of the medication, and the replenishment cost paid (minus any overhead and service fees charged by the pharmacy). Of course, the reimbursement 836 may be omitted if the cached replenishment coordination at steps 828 and 830 does not require reimbursement and/or reimbursement is prohibited by the qualified program and/or qualified entity.

A QPMM interfacing with a computer system and/or a COB system at the pharmacy can perform much, or all, of the method 800. The QPMM can monitor 814 disbursements of medication, track 816 qualified disbursements, determine 818 whether replenishment is needed, and/or access 826 replenishment information to coordinate completion of a cached replenishment. The QPMM can coordinate completion of a cached replenishment by coordinating payment 828 for a cached replenishment container and coordinating delayed shipment 830 of the cached replenishment container. The QPMM can also perform reporting 834 and/or reimbursing a qualified entity 838. The QPMM can also, where possible, identify 820 any alternative replenishment medication and modify 822 and store 824 new replenishment information for the identified alternative medication.

Prepurchased Replenishment

Some suppliers may offer advantageous discount pricing, which can be even lower than qualified discount plan pricing. A prepurchased replenishment model can enable a health care provider, a pharmacy, and/or a patient to enjoy greater cost savings by more fully taking advantage of advantageous discount pricing.

Advantageous discount pricing is typically offered only at certain times (e.g. at the end of the quarter, end of the month, etc.) and typically for a relatively short duration, such as one or two weeks at a time. These periods of limited duration advantageous pricing may be offered to 'blow-out' excess inventory, among other reasons. The discounts can be significant; often a fraction of the regular price, and often lower than even qualified discount plan prices. The replenishment functionality of a QPMM may be configured to identify such discounts and take advantage of them when they are available and when permitted by the regulations of a qualified program.

When an advantageous pricing situation is identified, replenishment containers are purchased by qualified entities based on predicted and/or forecasted future needs of a corresponding contracted pharmacy. The replenishment containers are 'prepurchased' in that shipment of the replenishment containers does not take place at the time of purchase, but rather shipment of the replenishment containers is delayed until a replenishment threshold for the medication is reached at the pharmacy and actual replenishment is necessary to restore inventory levels.

Figure 9:
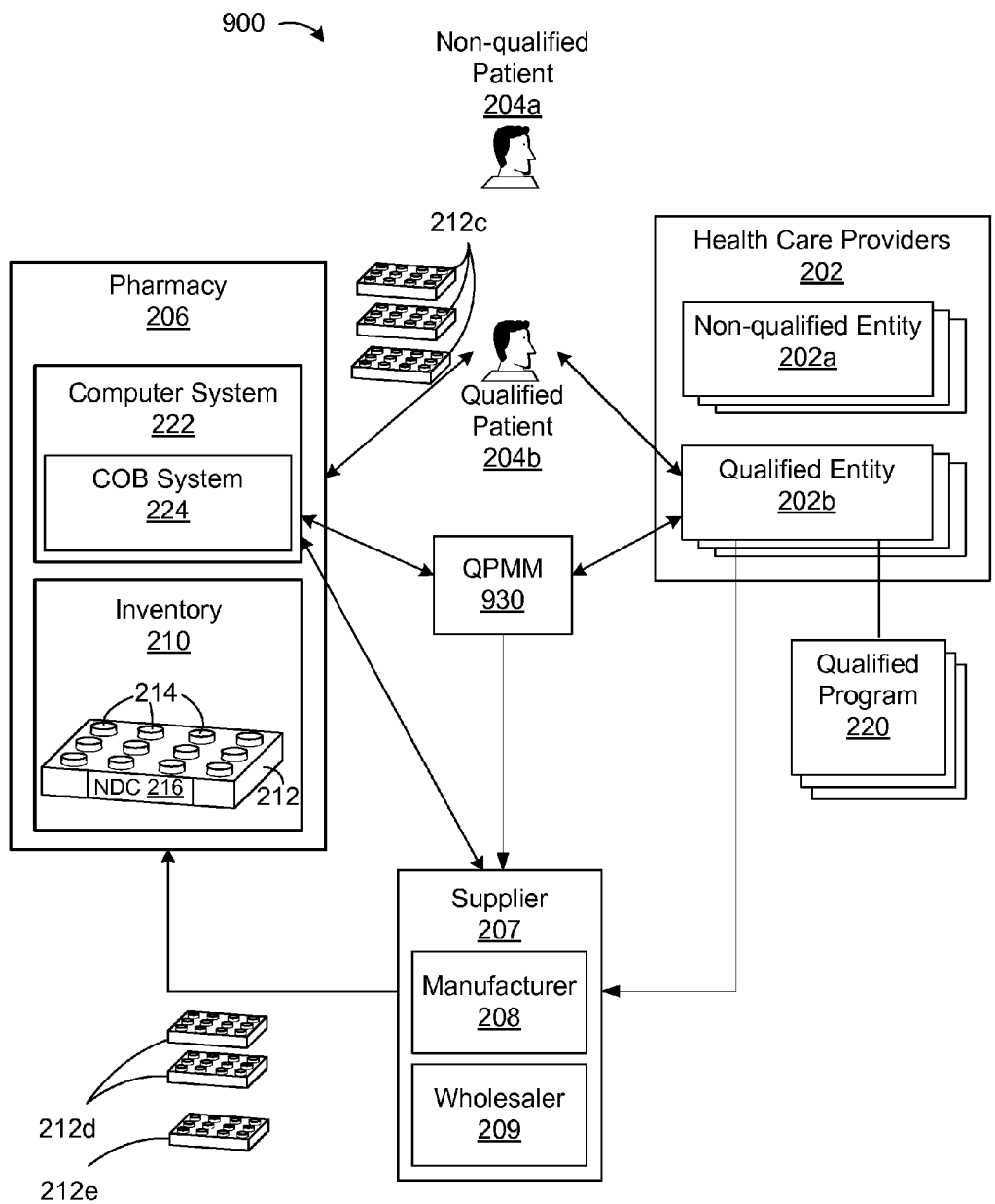
FIG. 9 is a block diagram of a system for dispersal of medications through a pharmacy and for restocking and prepurchased replenishment of disbursed inventory, the diagram depicting prepurchased replenishment.

FIG. 9 is a block diagram of another embodiment a system 900 for dispersal of medications through a pharmacy 206. The system 900 enables restocking and prepurchased replenishment of disbursed inventory. The diagram portrays the interactions between participants in a prepurchased replenishment scenario. The system 900 comprises a QPMM 930 that includes a system and/or method of prepurchased replenishment. As before, the pharmacy 206 disburses to patients 204 of health care providers 202. The health care providers 202 can include both non-qualified entities 202*a* and qualified entities 202*b* and the patients 204 can include both non-qualified patients 204*a* and qualified patients 204*b*. The qualified entities 202*b* can be qualified under, and participate in, one or more qualified programs 220.

In a prepurchased replenishment scenario, as portrayed in FIG. 9, the pharmacy 206 stocks a medication 214 for disbursement to non-qualified patients 204*a* and qualified patients 204*b*. The QPMM 930 monitors disbursements and tracks qualified disbursements. As part of tracking qualified disbursements, the QPMM 930 may determine anticipated replenishment needs. For example, the pharmacy in the scenario of FIG. 9 may expect to disburse two hundred units of the medication 214 to qualified patients 204*b* during a given time period (e.g. a month, six weeks, a quarter). The QPMM 930 can forecast or calculate an estimated replenishment need for the period that roughly approximates the expected disbursements of the medication 214. Accordingly, in the scenario of FIG. 9 the QPMM 930 may forecast a replenishment need of two hundred units of the medication 214.

The QPMM 930 also identifies advantageous pricing situations for medications the pharmacy distributes and/or equivalents of those medications. When the QPMM 930 identifies an advantageous pricing situation for a medication 214, the QPMM 930 coordinates a prepurchased replenishment transaction. The QPMM 930 coordinates a prepurchased replenishment by coordinating a purchase of replenishment containers 212 and ensuring that shipment of the replenishment containers 212 is delayed until replenishment is needed to replace inventory of the pharmacy that is disbursed as qualified disbursements. The number of replenishment containers 212 purchased is based on the forecasted need for a period. The prepurchased replenishment purchase is coordinated by arranging for payment from one or more qualified entities 202b and delayed shipment of the purchased replenishment containers from the supplier 207 to the pharmacy 206.

For the scenario of FIG. 9, the QPMM 930 may identify an advantageous pricing scenario in which containers of one hundred units of medication 214 are advantageously priced. Accordingly, the QPMM 930 can coordinate a prepurchased replenishment transaction in which two containers of one hundred are pre-purchased. The two containers of one hundred are purchased to cover the forecasted need of two hundred units to disburse as qualified disbursements during a given period of time. The two containers are not shipped at the time of the purchase. Rather, shipment is delayed until replenishment is needed to restore inventory levels due to qualified disbursements.

At some time after the prepurchased replenishment transaction, the pharmacy 206 may make qualified disbursements. For sake of illustration, consider if the actual need exceeds the forecasted need in the scenario of FIG. 9. Rather than only two hundred medication units 214 being disbursed as qualified disbursements, three hundred medication units 214 are disbursed as qualified disbursements to qualified patients 204b. Three containers 212c of one hundred medication units 214 can be disbursed.

In the scenario of FIG. 9, a replenishment threshold of two hundred medication units 214 may be established. Accordingly, when three hundred medication units 214 are disbursed as qualified disbursements, the replenishment threshold is reached and replenishment is needed to restore pharmacy inventory levels. The QPMM 930 can coordinate a replenishment order.

When the supplier 207 receives the replenishment order, the number of prepurchased replenishment containers that were pre-purchased, up to but not exceeding the total number of replenishment containers ordered, are then shipped to the pharmacy 206. Consider when two replenishment containers are pre-purchased consistent with prepurchased replenishment, as in the scenario of FIG. 9. If a replenishment order were to request only one container, one of the prepurchased replenishment containers is shipped as a replenishment container 212d. The qualified entity has pre-purchased the container at the advantageous pricing, and thus no payments are necessary for the replenishment order. In this manner, the qualified entity and/or pharmacy are able to more fully take advantage of discount pricing. For a subsequent order of one container, the second prepurchased replenishment container is shipped as replenishment container 212d, and again the qualified entity need pay nothing because the prepurchased replenishment container was pre-purchased.

For a replenishment order that exceeds the number of prepurchased replenishment containers that have been pre-purchased, the number of pre-purchased containers is subtracted from the total number of replenishment containers ordered. The qualified entity pays for additional replenishment containers to make up the difference. These additional replenishment containers are purchased at regular qualified discount pricing rather than advantageous pricing. All of the prepurchased replenishment containers are shipped as well as the additional replenishment containers purchased.

Turning again to the scenario of FIG. 9, the three hundred medication units 214 disbursed as qualified disbursements can be replenished by three replenishment containers of one hundred medication units. A replenishment order of three containers exceeds the two prepurchased replenishment containers that were pre-purchased. Accordingly, both of the prepurchased replenishment containers are shipped to the pharmacy as replenishment containers 212d. One additional replenishment container is shipped 212e to cover the total replenishment order. The QPMM coordinates the replenishment transaction for the additional replenishment container 212e. The qualified entity 202b pays the current qualified discount price for the additional replenishment container 212e, but has achieved greater cost savings by paying only the advantageous price for the two prepurchased replenishment containers shipped as replenishment containers 212d. The desired outcome is achieved. The pharmacy disbursed three total containers to qualified patients, and received three total replenishment containers. The pharmacy paid a lower price for at least some of the containers. Again, the result is accomplished without modification to the normal functioning of a computer system 222, or a COB system 224, that is already in use at a pharmacy.

As described previously, a prepurchased replenishment transaction can be coordinated by the QPMM 930. The QPMM 930 can also coordinate a subsequent replenishment order by coordinating payments from the qualified entities 202b and shipment to the pharmacy 206 by the supplier 207. To facilitate prepurchased replenishment, while accommodating traditional replenishment for additional replenishment containers, the QPMM 930 can track prepurchased replenishments and appropriately reduce traditional replenishment orders according to prepurchased replenishments. In this manner, the QPMM 930 can coordinate appropriate payments from the qualified entity and avert overpayments by the qualified entity.

A person having ordinary skill will appreciate that the QPMM can coordinate the actual replenishment order consistent with a traditional replenishment model or consistent with a cached replenishment model. In the case of traditional replenishment, shipment of the replenishment containers would occur when the replenishment order is received, as just described. In the case of cached replenishment, the prepurchased replenishment containers may be converted to cached replenishment containers upon receipt of a replenishment order.

As can be appreciated, coordinating delayed shipment of a prepurchased replenishment container can be accomplished a variety of ways. For example, the prepurchased replenishment container may be an actual container 212 which is purchased on behalf of the pharmacy. Shipment of the container however, is delayed until a replenishment order is received from the pharmacy. The supplier 207 reserves, or sets aside, the container 212 until a replenishment order is received for that medication 214. When the replenishment order is received, the supplier subtracts the total number of containers 212 ordered by the total number of prepurchased replenishment containers 212 reserved, or set aside, for the pharmacy 206.

In another embodiment, the prepurchased replenishment container may be "virtual" in that it is stored and tracked electronically by a computer system at the supplier 207. The prepurchased replenishment container then corresponds to an actual replenishment container that is reserved or set aside for the pharmacy. In still another embodiment, a computer system at the supplier 207 may track a prepurchased replenishment container as a special type of credit. The computer system creates (or indicates to the supplier to create) a prepurchased replenishment credit to the pharmacy 206. The prepurchased replenishment credit is for a replenishment container of medication credited to the pharmacy 206. Rather than crediting a dollar amount, the prepurchased replenishment credit is for a replenishment container. In this manner the desired advantageous pricing can be obtained for purchasing the prepurchased replenishment container.

The QPMM 930 can coordinate a prepurchased replenishment with a supplier 207 in a variety of ways. The QPMM 930 can generate a hardcopy (e.g. paper) prepurchased replenishment request that is sent to the supplier 207. In another embodiment, the QPMM 630 generates an electronic prepurchased replenishment request that is communicated to a computer system (not shown) of a supplier 207. The computer system of the supplier 207 can process the electronic request automatically. In still another embodiment, the QPMM 930 has permission to access a database of the supplier 207, and the QPMM 930 can generate a delayed shipment of a prepurchased replenishment container to a pharmacy by directly manipulating data in the supplier database. In still another embodiment, the QPMM 930 can coordinate a prepurchased replenishment order by notifying an operator through an output device (not shown). The output device may include a monitor or display running a suitable graphical user interface to thereby notify a user. Notifications can also be performed through a variety of other techniques including but not limited to email, updating a record in a database, a hardcopy print-out updating a spreadsheet, facsimile, telephone call, SMS text message, and the like.

The QPMM 930 can coordinate a prepurchased replenishment with a qualified entity 202b in much the same way as coordinating a typical replenishment or a cached replenishment. The QPMM 930 can send payment instructions to the qualified entity 202b. In still another embodiment, the QPMM 930 can coordinate a prepurchased replenishment entirely through a qualified entity 202b by providing the qualified entity 202b with payment instructions, as well as information to send with payment to the supplier 207 to request delayed shipment of a prepurchased replenishment container to the appropriate pharmacy 206 in exchange for the payment.

Figure 10A:
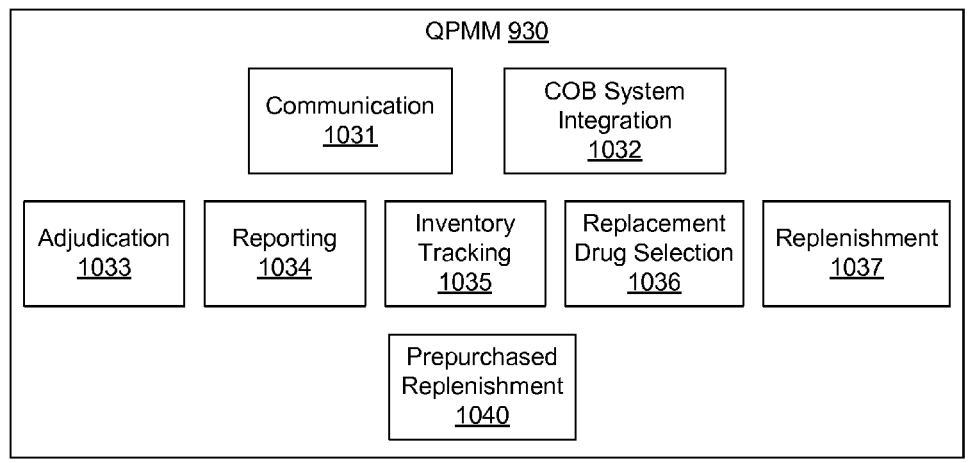
FIG. 10A is a block diagram of an embodiment of a QPMM that can enable a pharmacy to implement a prepurchased replenishment model.

FIG. 10A is a block diagram of an embodiment of a QPMM 930 that can enable a pharmacy to implement a prepurchased replenishment model. The QPMM 930 can comprise a communications module 1031, a COB system integration module 1032, an adjudication module 1033, a reporting module 1034, an inventory tracking module 1035, a replacement drug selection module 1036, a replenishment module 1037, and a prepurchased replenishment module. The communications module 1031, the COB system integration module 1032, the adjudication module 1033, the reporting module 1034, the inventory tracking module 1035, and the replenishment module 1037 can each operate similar to the corresponding modules of the QPMM 230 as described above with reference to FIG. 4A. The prepurchased replenishment module 1040, in combination with inventory tracking module 1035, the replacement drug selection module 1036, and/or the replenishment module 1037, enables replenishment via a prepurchased replenishment model.

The replacement drug selection module 1036 can identify advantageous pricing situations by various monitoring activities, including but not limited to monitoring supplier price lists, supplier databases, industry publications, and electronic communications. The QPMM 930 can also be notified of advantageous pricing by a pharmacy or a health care provider. Using the NDC, the replacement drug selection module 1036 may determine one or more equivalent medications to the dispensed medication. An equivalent medication may have a different NDC number than the medication dispensed to the patient 104, but may be chemically and biologically equivalent (e.g., the same medication produced by a different manufacturer). The replacement drug selection module 1036 may determine whether there would be pricing advantages to replenishing the pharmacy with the alternative medications and/or whether the qualified program is able to purchase the alternative medication. If so, the replacement drug selection module 1036 may present the option to the prepurchased replenishment module 1040 as an advantageous pricing situation.

The prepurchased replenishment module 1040 coordinates a prepurchased replenishment transaction with a qualified entity and a supplier. The prepurchased replenishment module 1040 can track the inventory that the pharmacy "loans" to various qualified entities as the pharmacy disburses medication to qualified patients of the qualified entities. Since the QPMM 930 is communicatively coupled to the systems of the pharmacy (e.g., coupled to the COB systems of the pharmacy), the prepurchased replenishment module 1040 may monitor the national drug code (NDC) of the medication disbursed to the patients of the qualified entities. Using the tracking information, the prepurchased replenishment module 1040 can forecast an estimated future need. The prepurchased replenishment module 1040 may forecast needs based on an average number of units of medication sold during a given period. The prepurchased replenishment module 1040 may track seasonal variations (e.g., cold and flu medications during winter months, allergy medications during spring and summer months). In another embodiment, the prepurchased replenishment module 1040 may forecast needs by using the tracking information to access a table or database.

Once a forecasted need and an advantageous pricing situation are identified, the prepurchased replenishment module 1040 can coordinate pre-purchase of the forecasted needs of the pharmacy by the qualified entities. The prepurchased replenishment module 1040 can coordinate payments by one or more qualified entities to a supplier to purchase a delayed shipment of a prepurchased replenishment container to the pharmacy. The supplier recognizes and reserves a prepurchased replenishment container for the pharmacy and delays shipment of the container to the pharmacy until an actual replenishment order is received. When an actual replenishment order for the medication is received from the pharmacy, the replenishment container is shipped to the pharmacy. The supplier can deduct the number of prepurchased replenishment containers from the total number of containers of medication ordered by the pharmacy and coordinate a replenishment transaction for the remaining number of containers. In this manner, the qualified entities can achieve greater cost savings by taking advantage of advantageous pricing.

In another embodiment, the prepurchased replenishment module coordinates a prepurchased replenishment by coordinating the generation of a prepurchased replenishment credit. The prepurchased replenishment credit can be a special type of credit for a replenishment container rather than for a paid amount. Accordingly, the supplier will offset a future replenishment order by a container rather than by a paid dollar amount. In still another embodiment an actual physical container is purchased on behalf of the pharmacy and set aside.

Figure 10B:
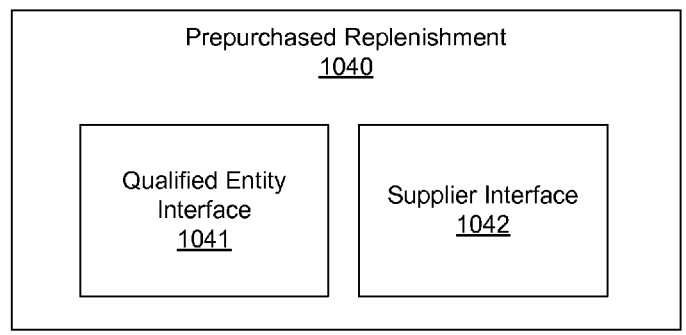
FIG. 10B is a block diagram of one embodiment of a prepurchased replenishment module configured to implement a prepurchased replenishment model.

FIG. 10B is a block diagram of one embodiment of a prepurchased replenishment module 1040 configured to coordinate prepurchased replenishment transactions. The prepurchased replenishment module 1040 can include a qualified entity interface module 1041 and a supplier interface module 1042. The qualified entity interface module 1041 can coordinate payments from qualified entities to suppliers for prepurchased replenishment orders. The qualified entity interface module 1041 can be configured to coordinate such payments in a variety of prescribed methods as may be necessary to comply with the requirements of one or more qualified discount programs. Moreover, the qualified entity interface module 1041 can be configured to coordinate payments in a variety of methods as may be necessary to interface with the protocols and methods of a variety of qualified entities, since these protocols and methods may vary from among qualified entities. For example, some qualified entities may receive electronic communications providing cached replenishment order information and payment instructions, whereas other qualified entities may require receipt of a hard copy document before payments will be processed.

The supplier interface module 1042 can coordinate prepurchased replenishment orders with suppliers. The supplier interface module 1042 can be configured to place prepurchased replenishment orders in a variety of prescribed methods as may be necessary to comply with the requirements of one or more qualified discount programs. Moreover, the supplier interface module 1040 can be configured to place prepurchased replenishment orders in a variety of methods as may be necessary to interface with the protocols and methods of a variety of suppliers, since these protocols and methods may vary among suppliers. For example, some suppliers may receive electronic communications that include a prepurchased replenishment order, whereas other qualified entities may require receipt of a hard copy document before a prepurchased replenishment order will be processed. Still other suppliers may allow a the QPMM 930 to directly access the a computer system and/or database at the supplier. The QPMM 930 can manipulate the data in the computer system and/or database at the supplier to reflect a cached replenishment credit.

Figure 11:
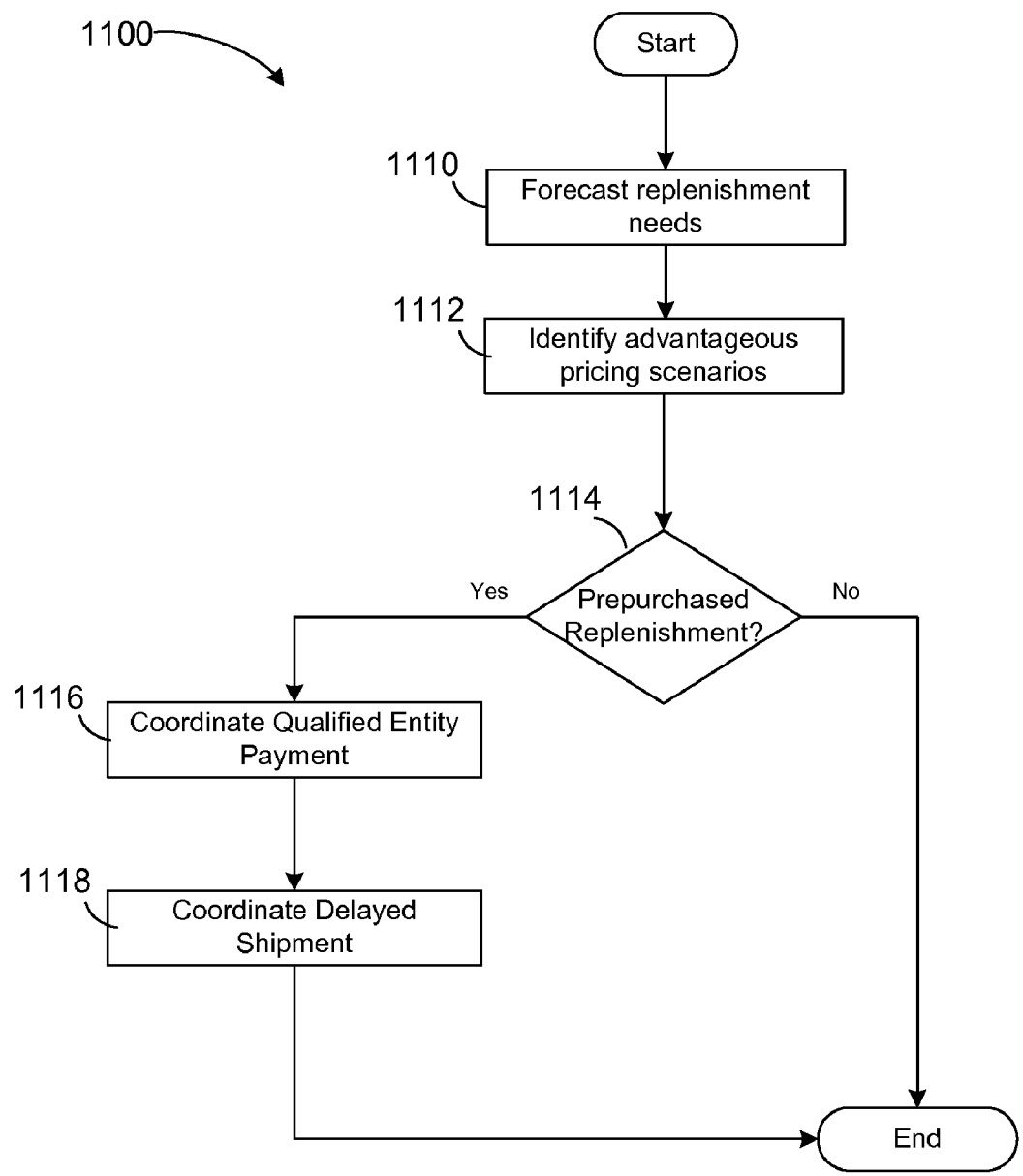
FIG. 11 is a flow chart of a method for prepurchased replenishment of pharmaceuticals.

FIG. 11 is a flow chart of a method 1100 for prepurchased replenishment of pharmaceuticals. The method 1100 forecasts 1110 the replenishment needs of the pharmacy for a given period of time. A forecast of the estimated replenishment needs of the pharmacy can be derived by monitoring disbursements of medication to qualified and/or non-qualified patients and tracking the number of qualified disbursements. Monitoring can occur by interfacing with the computer system and/or the COB system at the pharmacy. Interfacing with the COB system can be accomplished directly and/or by accessing one or more COB data structures. Information gathered by tracking the qualified disbursements can be used to derive disbursement patterns and to predict, or project, future disbursements. The projected future disbursements can be used to identify or forecast estimated needs.

The method 1100 can also identify 1112 advantageous pricing situations. The advantageous pricing situations can be identified 1112 by various monitoring activities, including but not limited to monitoring supplier price lists, supplier databases, electronic communications, industry publications, and electronic communications such as email and SMS text messages. Using the NDC for medication stocked at a pharmacy, the method can also determine one or more equivalent medications to the stocked medication. An equivalent medication may have a different NDC number than the medication dispensed to a patient, but may be chemically and biologically equivalent (e.g., the same medication produced by a different manufacturer, a different size container or other packaging). The nature of the qualified entity and/or the qualified program may determine whether a particular discounted medication is available. If an acceptable lower-cost alternative is found, the new replenishment information, including the alternative NDC and supplier information, may be recorded 822. The method 1100, when identifying 1112 advantageous pricing, may determine whether there would be pricing advantages to replenishing the pharmacy with the alternative medications and/or whether the qualified program allows purchase of the alternative medication. Information about the advantageous pricing situation can be stored in a COB data structure for use in coordinating a prepurchased replenishment transaction. The stored information may be stored in the pharmacy's COB system and can include information relating to the qualified entity, qualified program, and/or alternative replenishment NDC.

With a forecast of replenishment needs and an advantageous pricing situation identified, the method 1100 can determine 1114 whether to coordinate a prepurchased replenishment transaction. As part of the determination, the method 1100 may consider whether the advantageous pricing situation is still in effect. Moreover, the method 1100 may consider the actual inventory of the pharmacy in relation to the estimate of replenishment needs. The method 1114 may also consider whether prepurchased replenishment is possible under the requirements of one or more qualified plans under which the pharmacy makes qualified disbursements. If the method 1100 determines 1114 that prepurchased replenishment should not occur, the method can end. If the method 1100 determines that prepurchased replenishment should occur, flow continues to coordinate the cached replenishment transaction.

The method 1100 can coordinate a prepurchased replenishment transaction in two parts: by coordinating 1116 payments for the replenishment containers by qualified entities to the supplier, and coordinating 1118 delayed shipment of the replenishment containers by the supplier. To coordinate 1116 payments the method 1100 can use replenishment information that may be stored in a COB data structure. The replenishment information can include, but is not limited to, contact information for the qualified entity, preferred and/or accepted forms of communication with the qualified entity, and protocols and procedures followed by (or for interfacing with) the qualified entity. The replenishment information can further include pricing and quantity information, as well as qualified plan information. Coordination of payment may include electronic communication and/or hard copy communication to the qualified entity. The communication can outline instructions and terms for payment to the supplier. In another embodiment, the communication to the qualified entity can be an invoice sent on behalf of the supplier containing information regarding the shipment of the replenishment order. In another embodiment, coordination of payment may comprise providing the supplier with information as to how to directly bill the qualified entity for a replenishment shipment to a pharmacy.

The method 1100 can also use replenishment information stored in a COB data structure to coordinate 1118 delayed shipment of the replenishment container to the pharmacy. The replenishment information can include, but is not limited to contact information for the supplier, protocols and forms of communication accepted by the supplier, the pharmacy shipping address, preferred and/or accepted forms of shipment, preferred and/or accepted forms of communication with the pharmacy, protocols and procedures for interfacing with the pharmacy, and quantity and packaging information. The shipment from the supplier to the pharmacy is delayed until such time as the pharmacy necessitates an actual replenishment and places a replenishment order with the supplier for the same medication that was pre-purchased. As can be appreciated, the delayed shipping can be accomplished a variety of ways, including but not limited to a request to hold shipment, instructions regarding delay of shipment, instructions to delay filling the prepurchased replenishment order, generation of a special type of credit for a prepurchased replenishment container, and reserving a physical container for later shipment.

In another embodiment, coordination 1116 of qualified entity payments and coordination 1118 of delayed shipment of prepurchased replenishment containers can be accomplished in a single step. For example, the communication to the supplier can include instructions and information for the supplier to directly bill the qualified entity for a replenishment shipment. As another example, the communication to the qualified entity can include instructions to pass on to the supplier to instruct the supplier to delay shipment of the prepurchased replenishment containers.

A QPMM interfacing with a computer system and/or a COB system at the pharmacy can perform much, or all, of the method 1100. The QPMM can monitor disbursements of medication and track qualified disbursements to forecast whether replenishment is needed. The QPMM can identify advantageous pricing situations by monitoring pricing via a computer network or electronic communication with computer systems at the supplier. The QPMM can coordinate completion of a prepurchased replenishment by coordinating payment 1116 for a prepurchased replenishment container and coordinating delayed shipment 1118 of the cached replenishment container.

Figure 12:
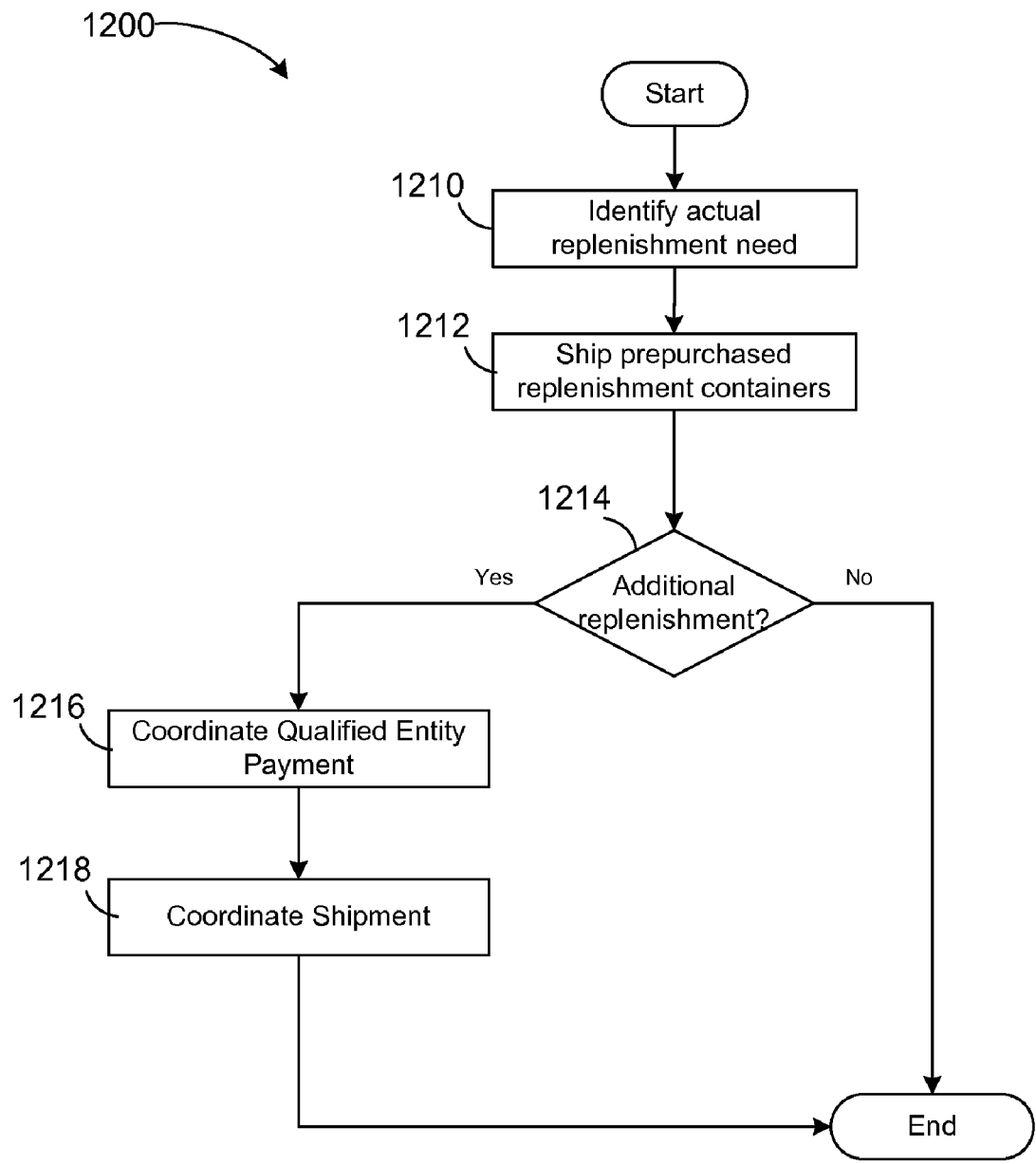
FIG. 12 is a flow chart of a method for replenishment of pharmaceuticals beyond a quantity replenished by prepurchased replenishment.

FIG. 12 is a flow chart of a method 1200 for replenishment of pharmaceuticals beyond a quantity replenished by prepurchased replenishment. When a replenishment threshold is reached (i.e. the number of qualified disbursements to qualified patients meets or exceeds a replenishment threshold), actual replenishment is needed. The method 1200 identifies 1210 the number of containers the pharmacy needs replenished based on the number of qualified disbursements. This number may be referred to as the actual replenishment need of the pharmacy. The method 1200 can then ship 1212 the number of replenishment containers that correspond to the number of prepurchased replenishment containers purchased, up to but not exceeding the actual replenishment need. Once the prepurchased replenishment containers are shipped, the method can determine 1214 whether additional replenishment is needed, based on the actual replenishment need as compared to the number of prepurchased replenishment containers purchased. If no additional replenishment is needed, the method can end. If additional replenishment is needed, the method 1200 can coordinate the additional replenishment by coordinating 1216 payment by a qualified entity and coordinating 1218 shipment to the pharmacy.

Figure 13:
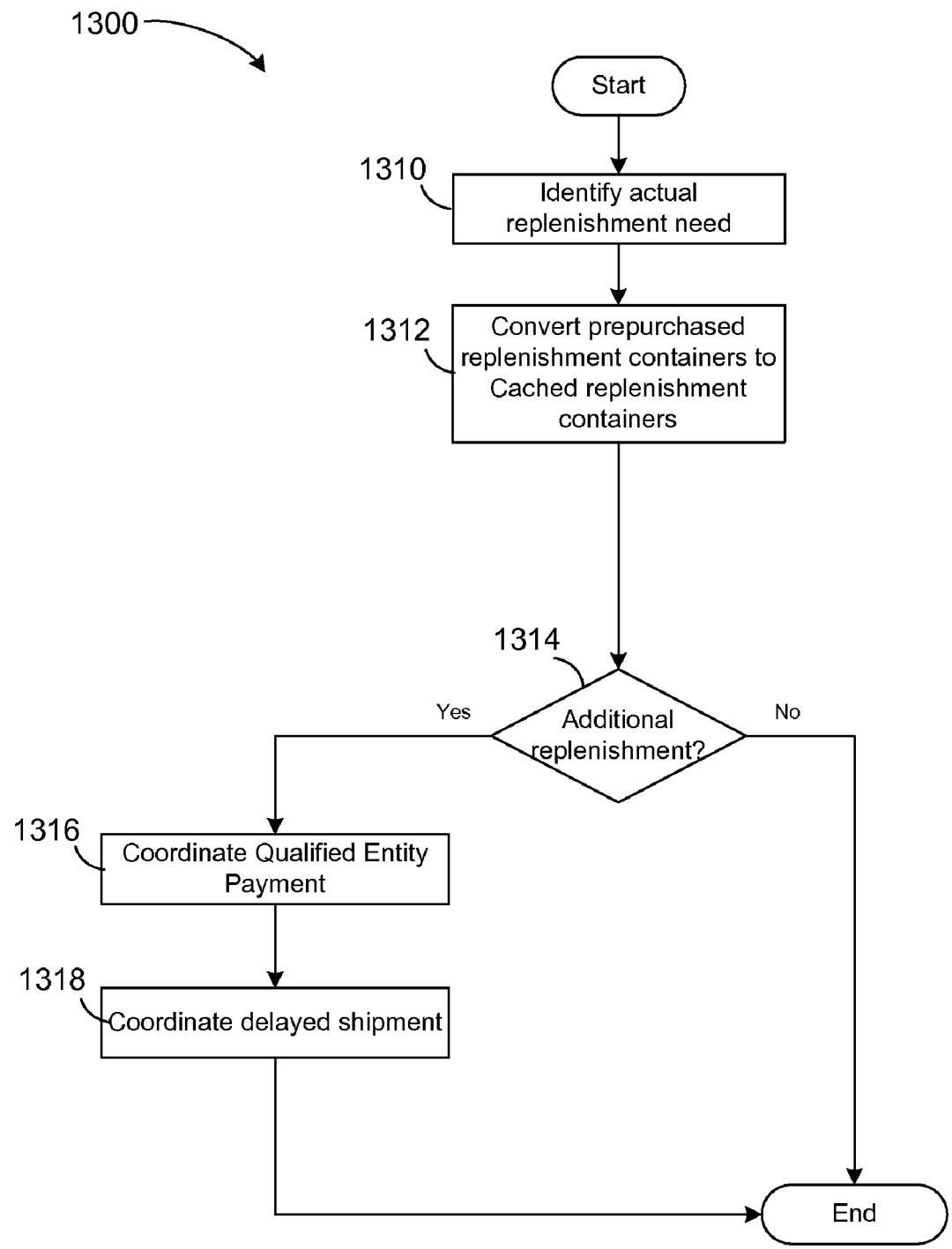
FIG. 13 is a flow chart of a method for cached replenishment of pharmaceuticals in conjunction with prepurchased replenishment.

FIG. 13 is a flow chart of a method 1300 for cached replenishment of pharmaceuticals in conjunction with prepurchased replenishment. When a replenishment threshold is reached (i.e. the number of qualified disbursements to qualified patients meets or exceeds a replenishment threshold), actual replenishment is needed. The method 1300 identifies 1310 the number of containers the pharmacy needs replenished based on the number of qualified disbursements. This number may be referred to as the actual replenishment need of the pharmacy. The method 1300 then converts prepurchased replenishment containers into cached replenishment containers, up to but not exceeding the actual replenishment need. Once the prepurchased replenishment containers are converted to cached replenishment containers, the method can determine 1314 whether additional replenishment is needed, based on the actual replenishment need as compared to the number of prepurchased replenishment containers purchased. If no additional replenishment is needed, the method can end. If additional replenishment is needed, the method 1300 can coordinate the additional cached replenishment by coordinating 1316 payment by a qualified entity and coordinating 1318 delayed shipment to the pharmacy. The method then ends.

Consistent with cached replenishment as described above, once the number of disbursed medication units reaches a replacement threshold, the pharmacy computer system may place a restocking order. The number of containers ordered in the restocking order can be reduced by the number of cached replenishment containers associated with the pharmacy. The cached replenishment containers are shipped and any additional replacement containers requested are also shipped. The pharmacy is only charged for the additional replacement containers, beyond the number of cached replenishment containers shipped.

It will be obvious to those having skill in the art that many changes may be made to the details of the above-described embodiments without departing from the underlying principles of the disclosure.

What is claimed is:

1. A computer system to enable a pharmacy that disburses medications to patients of a plurality of health care providers to automatically coordinate prepurchased replenishment of medications disbursed to qualified patients of one or more qualified entities under a qualified discount program, the system comprising:
    a processor; and
    a memory in electrical communication with the processor, the memory including,
        an operating system, and
        a prepurchased replenishment module to perform the method of
            monitoring disbursements of medication units by the pharmacy to patients of the plurality of health care providers, wherein one or more of the plurality of health care providers are qualified entities, wherein each qualified entity is eligible to participate in one or more qualified discount programs which provide purchasing of medications at or below a predetermined ceiling price, and wherein the qualified entities may purchase the medication units for no more than a qualified discount medication price under at least one of the one or more qualified discount programs;
            determining which of the disbursements of medication units are qualified disbursements to qualified patients of the one or more qualified entities under the one or more qualified discount programs, wherein the qualified patients are the only patients eligible by regulation to receive medications under the qualified discount program;
            tracking the number of medications disbursed through qualified disbursements;
            placing a replenishment order for one or more replenishment containers from a supplier when the number of medication units disbursed through qualified disbursements reaches a replenishment threshold;
            forecasting future disbursements of medication units during a given time period by the pharmacy to qualified patients of the one or more qualified entities;
            receiving price information from suppliers, wherein the price information comprises pricing scenarios for the medication units, and wherein each pricing scenario comprises an offer to sell medication units at a predetermined price;
            monitoring the pricing scenarios for the medication units wherein the monitored pricing scenarios are offered under the one or more qualified discount drug programs;

identifying an advantageous pricing scenario for the medication units from among the monitored pricing scenarios, wherein the identified advantageous pricing scenario comprises an offer to sell medication units at an advantageous price less than the qualified discount medication price;

coordinating a purchase of a prepurchased replenishment container from a supplier, wherein the prepurchased replenishment container is purchased at the advantageous price of the identified advantageous pricing scenario;

coordinating delayed shipment of the prepurchased replenishment container by the supplier to the pharmacy at least until the replenishment order is placed; and associating the prepurchased replenishment container with the pharmacy, wherein the prepurchased replenishment container and one less than the number of replenishment containers ordered are shipped to the pharmacy in response to the replenishment order.

2. The computer system of claim 1, wherein the method performed by the prepurchased replenishment module further comprises:

identifying an actual replenishment need at the pharmacy of at least one replenishment container;

coordinating shipment of an actual replenishment container corresponding to the prepurchased replenishment container to the pharmacy by the supplier; and reducing by one container the number of replenishment containers ordered in a replenishment order of the pharmacy to the supplier for the shipped actual replenishment container.

3. The computer system of claim 2, wherein the method performed by the prepurchased replenishment module further comprises coordinating actual replenishment for the number of replenishment containers remaining in the order of the pharmacy after the number of containers ordered is reduced for the shipped actual replenishment container.

4. The computer system of claim 2, wherein identifying an actual replenishment need comprises:

monitoring disbursements of medication units by the pharmacy to patients of a plurality of health care providers; and tracking the number of medication units disbursed through qualified disbursements to qualified patients of qualified entities under a qualified discount program.

5. The computer system of claim 4, wherein monitoring disbursements of medication units by the pharmacy comprises reading bar codes that correspond to the disbursed medication units.

6. The computer system of claim 4, wherein monitoring the disbursement by the pharmacy of medication units to patients of the plurality of health care providers includes communicating with the health care providers over a network.

7. The computer system of claim 1, wherein coordinating the purchase of the prepurchased replenishment container further comprises coordinating payment directly to the supplier for the purchase by the one or more qualified entities.

8. The computer system of claim 1, wherein the method performed by the prepurchased replenishment module further comprises determining a share of cost for each of two or more qualified entities for the prepurchased replenishment container based on the number of medication units disbursed to qualified patients of each qualified entity.

9. The computer system of claim 8, wherein the method performed by the prepurchased replenishment module further comprises generating an invoice for each qualified entity, each invoice reflecting a corresponding share of cost.

10. The computer system of claim 1, further comprising an output device in electrical communication with the processor and wherein the method performed by the prepurchased replenishment module further comprises instructing the output device to provide notification of an advantageous pricing scenario to a user.

11. The computer system of claim 1, wherein forecasting future disbursements comprises:

monitoring disbursements of medication units by the pharmacy to patients of a plurality of health care providers;

tracking the number of medication units disbursed through qualified disbursements to qualified patients of qualified entities under a qualified discount program; and calculating an average number of medication units disbursed through qualified disbursements during a given time period.

12. A non-transitory computer readable storage medium, having stored thereon computer readable instruction code for a computer system to perform a method of automatic prepurchased replenishment of medications disbursed by a pharmacy to qualified patients of one or more qualified entities under a qualified discount program, the method comprising:

monitoring disbursements of medication units by the pharmacy to patients of a plurality of health care providers, wherein one or more of the plurality of health care providers are qualified entities, wherein each qualified entity is eligible to participate in one or more qualified discount programs which provide purchasing of medications at or below a predetermined ceiling price, and wherein the qualified entities may purchase the medication units for no more than a qualified discount medication price under at least one of the one or more qualified discount programs;

determining which of the disbursements of medication units are qualified disbursements to qualified patients of the one or more qualified entities under the one or more qualified discount programs, wherein the qualified patients are the only patients eligible by regulation to receive medications under the qualified discount program;

tracking the number of medications disbursed through qualified disbursements;

placing a replenishment order for one or more replenishment containers from a supplier when the number of medication units disbursed through qualified disbursements reaches a replenishment threshold;

forecasting future disbursements of medication units during a given time period by the pharmacy to qualified patients of the one or more qualified entities;

receiving price information from suppliers, wherein the price information comprises pricing scenarios for the medication units, and wherein each pricing scenario comprises an offer to sell medication units at a predetermined price;

monitoring the pricing scenarios for the medication units, wherein the monitored pricing scenarios are offered under the one or more qualified discount drug programs;

identifying an advantageous pricing scenario for the medication units from among the monitored pricing scenarios, wherein the identified advantageous pricing scenario comprises an offer to sell medication units at an advantageous price less than the qualified discount medication price;

coordinating a purchase of a prepurchased replenishment container from a medication supplier, wherein the prepurchased replenishment container is purchased at the advantageous price of the identified advantageous pricing scenario;

coordinating delayed shipment of the prepurchased replenishment container by the supplier to the pharmacy at least until the replenishment order is placed; and associating the prepurchased replenishment container with the pharmacy, wherein the prepurchased replenishment container and one less than the number of replenishment containers ordered are shipped to the pharmacy in response to the replenishment order.

13. The computer system of claim 12, wherein coordinating a purchase of a prepurchased replenishment container further comprises coordinating payment for the purchase by the one or more qualified entities directly to the supplier.

14. The computer readable storage medium of claim 12, wherein the method further comprises determining a share of cost for each of two or more qualified entities for the purchase of the prepurchased replenishment container.

15. The computer readable storage medium of claim 12, wherein the method further comprises:

identifying an actual replenishment need at the pharmacy of at least one replenishment container;

coordinating shipment of an actual replenishment container corresponding to the prepurchased replenishment container to the pharmacy by the supplier;

reducing by one container the number of replenishment containers ordered in a replenishment order of the pharmacy to the supplier for the shipped actual replenishment container; and coordinating actual replenishment for the number of replenishment containers remaining in the order of the pharmacy after the number of containers ordered is reduced for the shipped actual replenishment container.

16. The computer readable storage medium of claim 15, wherein identifying an actual replenishment need comprises:

monitoring disbursements of medication units by the pharmacy to patients of a plurality of health care providers; and tracking the number of medication units disbursed through qualified disbursements to qualified patients of the qualified entities under a qualified discount program.

17. The computer readable storage medium of claim 16, wherein monitoring disbursements by the pharmacy comprises reading bar codes that correspond to the disbursed medication units.

18. The computer readable storage medium of claim 16, wherein monitoring the disbursement by the pharmacy of medication units to patients of the plurality of health care providers includes communicating with the health care providers over a network.

19. The computer readable storage medium of claim 12, wherein the method further comprises instructing an output device in electrical communication with the computer system to provide notification of an advantageous pricing scenario to a user of the computer system.

20. The computer readable storage medium of claim 12, wherein forecasting future disbursements comprises:

monitoring disbursements of medication units by the pharmacy to patients of a plurality of health care providers;

tracking the number of medication units disbursed through qualified disbursements to qualified patients of qualified entities under a qualified discount program; and calculating an average number of medication units disbursed through qualified disbursements during the given time period.

21. A computer-implemented method to enable a pharmacy to disburse medications to patients of a plurality of health care providers and to automatically coordinate replenishment of medications dispersed by the pharmacy to qualified patients of one or more qualified entities under a discount plan, the method comprising:

a computer system monitoring disbursements of medication units by the pharmacy to patients of the plurality of health care providers, wherein one or more of the plurality of health care providers are qualified entities, wherein each qualified entity is eligible to participate in one or more qualified discount programs which provide purchasing of medications at or below a predetermined ceiling price, and wherein the qualified entities may purchase the medication units for no more than a qualified discount medication price under at least one of the one or more qualified discount programs;

the computer system determining which of the disbursements of medication units are qualified disbursements to qualified patients of the one or more qualified entities under the one or more qualified discount programs, wherein the qualified patients are the only patients eligible by regulation to receive medications under the qualified discount program;

the computer system tracking the number of medications disbursed through qualified disbursements;

the computer system initiating a replenishment order by the one or more qualified entities for one or more replenishment containers from a supplier when the number of medication units disbursed through qualified disbursements reaches a replenishment threshold;

the computer system forecasting future qualified disbursements of medication units during a given time period by the pharmacy to qualified patients of the one or more qualified entities;

the computer system receiving price information from suppliers, wherein the price information comprises pricing scenarios for the medication units, and wherein each pricing scenario comprises an offer to sell medication units at a predetermined price;

the computer system monitoring the pricing scenarios for the medication units, wherein the monitored pricing scenarios are offered under the one or more qualified discount drug programs;

the computer system identifying an advantageous pricing scenario for the medication units from among the monitored pricing scenarios, wherein the identified advantageous pricing scenario comprises an offer to sell medication units at a deeply discounted price less than the qualified discount medication price;

the computer system coordinating a purchase of a prepurchased replenishment container, wherein payment for the purchase is made to the supplier by the one or more qualified entities, and wherein the payment amount is the deeply discounted price of the identified advantageous pricing scenario;

the computer system coordinating delayed shipment of the prepurchased replenishment container by the supplier to the pharmacy at least until the replenishment order is initiated;

the computer system associating the prepurchased replenishment container with the pharmacy, wherein the prepurchased replenishment container and one less than the number of replenishment containers ordered are shipped to the pharmacy in response to the replenishment order.

22. The computer-implemented method of claim 21, wherein the computer system forecasting future qualified disbursements comprises:
the computer system monitoring disbursements of medication units by the pharmacy to patients of the plurality of health care providers; and
the computer system tracking the number of medication units dispensed through qualified dispersals to qualified patients of the one or more qualified entities.

23. The computer-implemented method of claim 22, wherein the computer system monitoring disbursements of medication units by the pharmacy comprises reading bar codes that correspond to the disbursed medication units.

24. The computer-implemented method of claim 22, wherein the computer system monitoring the disbursements of medication units by the pharmacy includes communicating with the health care providers over a network.

25. The computer-implemented method of claim 21, further comprising
the computer system coordinating shipment of an actual replenishment container corresponding to the prepurchased replenishment container to the pharmacy by the supplier; and
reducing by one container the number of replenishment containers ordered in a replenishment order of the pharmacy to the supplier for the shipped actual replenishment container.

26. The computer-implemented method of claim 21, wherein the computer system coordinating the purchase of the prepurchased replenishment container further comprises coordinating payment directly to the supplier for the purchase by the one or more qualified entities.

27. The computer-implemented method of claim 21, further comprising the computer system determining a share of cost for each of two or more qualified entities for the prepurchased replenishment container based on the number of medication units disbursed to qualified patients of each qualified entity.

28. The computer-implemented method of claim 27, further comprising the computer system generating an invoice for each qualified entity, each invoice reflecting a corresponding share of cost.

29. The computer-implemented method of claim 21, further comprising the computer system providing a notification of an advantageous pricing scenario to a user via an output device.

30. A computer system to enable a pharmacy to disburse medications to patients of a plurality of health care providers and to automatically coordinate replenishment of medications dispersed to qualified patients of one or more qualified entities under a discount plan, the system comprising:
a processor; and
a memory in electrical communication with the processor, the memory including,
an operating system;
a monitoring module to perform the method of:
monitoring disbursements of medication units by the pharmacy to patients of the plurality of health care providers, wherein one or more of the plurality of health care providers are qualified entities, wherein each qualified entity is eligible to participate in one or more qualified discount programs which provide purchasing of medications at or below a predetermined ceiling price, and wherein the qualified entities may purchase the medication units for no more than a qualified discount medication price under at least one of the one or more qualified discount programs;
determining which of the disbursements of medication units are qualified disbursements to qualified patients of the one or more qualified entities under the one or more qualified discount programs, wherein the qualified patients are the only patients eligible by regulation to receive medications under the qualified discount program; and
tracking the number of medication units dispensed through qualified dispersals to qualified patients of the one or more qualified entities;
a replenishment module to perform the method of,
determining when the number of medication units dispensed through qualified dispersals reaches a replenishment threshold; and
upon the number of medication units dispensed through qualified dispersals reaching the replenishment threshold, initiating a replenishment order by the one or more qualified entities for one or more replenishment containers from a supplier at the qualified discount medication price under the qualified program, the replenishment container ordered for shipment to the pharmacy; and
a prepurchased replenishment module to perform the method of:
forecasting future qualified disbursements of medication units during a given time period by the pharmacy to qualified patients of the one or more qualified entities;
receiving price information from suppliers, wherein the price information comprises pricing scenarios for the medication units, and wherein each pricing scenario comprises an offer to sell medication units at a predetermined price;
monitoring the pricing scenarios for the medication units, wherein the monitored pricing scenarios are offered under the one or more qualified discount drug programs;
identifying an advantageous pricing scenario for the medication units from among the monitored pricing scenarios, wherein the identified advantageous pricing scenario comprises an offer to sell medication units at a deeply discounted price less than the qualified discount medication price;
coordinating a purchase of a prepurchased replenishment container, wherein payment for the purchase is made to the supplier by the one or more qualified entities, and wherein the payment amount is the deeply discounted price of the identified advantageous pricing scenario;
coordinating delayed shipment of the prepurchased replenishment container by the supplier to the pharmacy at least until the replenishment order is initiated; and
associating the prepurchased replenishment container with the pharmacy,
wherein the prepurchased replenishment container and one less than the number of replenishment containers ordered are shipped to the pharmacy in response to the replenishment order.

* * * * *